(12) United States Patent
Ma

(10) Patent No.: US 10,590,386 B2
(45) Date of Patent: *Mar. 17, 2020

(54) METHODS AND COMPOSITIONS FOR PREPARING CARDIOMYOCYTES FROM STEM CELLS AND USES THEREOF

(71) Applicant: Insitute of Biophysics, Chinese Academy of Sciences, Beijing (CN)

(72) Inventor: Yue Ma, Beijing (CN)

(73) Assignee: INSITUTE OF BIOPHYSICS, CHINESE ACADEMY OF SCIENCES, Beijing (CN)

(*) Notice: Subject to any disclaimer, the term of this patent is extended or adjusted under 35 U.S.C. 154(b) by 0 days.

This patent is subject to a terminal disclaimer.

(21) Appl. No.: 14/925,829

(22) Filed: Oct. 28, 2015

(65) Prior Publication Data

US 2016/0122719 A1    May 5, 2016

Related U.S. Application Data

(63) Continuation of application No. 13/703,608, filed as application No. PCT/CN2010/078645 on Nov. 11, 2010, now Pat. No. 9,273,286.

(30) Foreign Application Priority Data

Jun. 13, 2010   (CN) .......................... 2010 1 0207603

(51) Int. Cl.
    *C12N 5/077*    (2010.01)

(52) U.S. Cl.
    CPC ...... *C12N 5/0657* (2013.01); *C12N 2501/115* (2013.01); *C12N 2501/155* (2013.01); *C12N 2501/16* (2013.01); *C12N 2501/385* (2013.01); *C12N 2501/415* (2013.01); *C12N 2506/02* (2013.01)

(58) Field of Classification Search
    CPC ............ C12N 5/0657; C12N 2501/155; C12N 2506/02; C12N 2501/415; C12N 2501/115; C12N 2501/16; C12N 2501/385
    See application file for complete search history.

(56) References Cited

U.S. PATENT DOCUMENTS

| 5,686,102 A | 11/1997 | Gross et al. |
| 5,736,154 A | 4/1998 | Fuisz |
| 5,741,511 A | 4/1998 | Cho et al. |
| 5,886,039 A | 3/1999 | Kock et al. |
| 5,941,868 A | 8/1999 | Kaplan et al. |
| 6,197,801 B1 | 3/2001 | Lin |
| 6,258,374 B1 | 7/2001 | Friess et al. |
| 6,800,480 B1 | 10/2004 | Bodnar et al. |
| 7,449,334 B2 | 11/2008 | Thomson et al. |
| 7,452,718 B2 | 11/2008 | Gold et al. |
| 7,727,762 B2 | 6/2010 | Fukuda et al. |
| 8,252,583 B2 | 8/2012 | Fukuda et al. |
| 8,951,798 B2 | 2/2015 | Palecek et al. |
| 9,273,286 B2 | 3/2016 | Ma |
| 2004/0106096 A1 | 6/2004 | Thomson et al. |
| 2005/0214939 A1 | 9/2005 | Gold |
| 2007/0134215 A1 | 6/2007 | Fukuda et al. |
| 2008/0038820 A1 | 2/2008 | Reil et al. |
| 2009/0269314 A1 | 10/2009 | Keller et al. |
| 2010/0166713 A1 | 7/2010 | Dalton et al. |
| 2013/0189785 A1 | 7/2013 | Palecek |
| 2015/0299658 A1 | 10/2015 | Ma |
| 2016/0122719 A1 | 5/2016 | Ma |

FOREIGN PATENT DOCUMENTS

| CA | 2395950 A1 | 7/2001 |
| CA | 2802526 A1 | 12/2011 |
| CN | 1863904 | 11/2006 |
| CN | 1969040 | 5/2007 |
| CN | 101074428 | 11/2007 |
| CN | 101641436 | 2/2010 |
| CN | 101720355 | 6/2010 |
| EP | 1 674 562 | 6/2006 |
| EP | 2580317 A1 | 4/2013 |
| EP | 2891712 A1 | 7/2015 |
| JP | 2003-526677 | 9/2003 |
| JP | 2006-517092 | 7/2006 |
| JP | 2006-523091 | 10/2006 |
| JP | 2007-532103 | 11/2007 |
| JP | 2009-524484 | 7/2009 |
| JP | 2009-171981 | 8/2009 |
| JP | 2009-531054 | 9/2009 |
| JP | 2009-535058 | 10/2009 |

(Continued)

OTHER PUBLICATIONS

Cao et al. "Transcriptional and functional profiling of human embryonic stem cell-derived cardiomyocytes."PLoS One. 2008;3(10):e3474. (Year: 2008).*
Hoon Lee et al. "Human Pluripotent Stem Cell-Derived Atrial and Ventricular Cardiomyocytes Develop from Distinct Mesoderm Populations."Cell Stem Cell. Aug. 3, 2017;21(2):179-194.e4. (Year: 2017).*
Rosenthal and Xavier-Neto. ".From the bottom of the heart: anteroposterior decisions in cardiac muscle differentiation." Curr Opin Cell Bio. Dec. 2000;12(6):742-6. (Year: 2002).*
Braam et al. "Prediction of drug-induced cardiotoxicity using human embryonic stem cell-derived cardionnyocytes."Stem Cell Res. Mar. 2010;4(2):107-16. Epub Dec. 3, 2009. (Year: 2009).*

(Continued)

*Primary Examiner* — Titilayo Moloye
(74) *Attorney, Agent, or Firm* — Rimon, P.C.

(57) ABSTRACT

The present invention discloses novel compositions and methods for enhancing cardiac differentiation efficiency of stem cells or promoting ventricular and atrial cardiomyocytes formation from stem cells. The present invention also discloses the atrial and ventricular cardiomyocytes formed from the stem cells, and the uses of the cardiomyocytes for repairing cardiac injuries and screening for new medicaments for treating cardiac injuries.

24 Claims, 5 Drawing Sheets
Specification includes a Sequence Listing.

(56) References Cited

FOREIGN PATENT DOCUMENTS

| | | |
|---|---|---|
| JP | 2010-508846 | 3/2010 |
| JP | 2011-517563 | 6/2011 |
| WO | WO-2001/068135 | 9/2001 |
| WO | 2002081729 A2 | 10/2002 |
| WO | WO-2004/050894 | 6/2004 |
| WO | WO-2004/081205 | 9/2004 |
| WO | WO-2004/098490 | 11/2004 |
| WO | WO-2005/033298 | 4/2005 |
| WO | WO-2005/098425 | 10/2005 |
| WO | WO-2007/087355 | 8/2007 |
| WO | WO-2007/113505 | 10/2007 |
| WO | WO-2007/130474 | 11/2007 |
| WO | WO-2008/054819 | 5/2008 |
| WO | WO-2008/060446 | 5/2008 |
| WO | WO-2008/112323 | 9/2008 |
| WO | WO-2009/036982 | 3/2009 |
| WO | WO-2009/075954 | 6/2009 |
| WO | WO-2010/007031 | 1/2010 |
| WO | WO-2011/157029 | 12/2011 |
| WO | WO-2013/056072 | 4/2013 |
| WO | WO-2013/159349 | 10/2013 |
| WO | WO-2014/015777 | 1/2014 |

OTHER PUBLICATIONS

Bao et al., "Regulation of chamber-specific gene expression in the developing heart by Irx4," Science (1999) 283:1161-1164.
Boheler et al., "Differentiation of pluripotent embryonic stem cells into cardiomyocytes," Circulation Research (2002) 91:189-201.
Broach, et al., "High throughput screening for drug discovery," Nature (1996) 384:14-16.
Burbaum, et al., "New technologies for high-throughput screening," Curr. Opin. Chem. Biol. (1997) I:72-78.
Cao et al., "Highly efficient induction and long-term maintenance of multipotent cardiovascular progenitors from human pluripotent stem cells under defined conditions," Cell Research (2013) 23:1119-1132.
Chambers, et al., "Functional expression cloning of Nanog, a pluripotency sustaining factor in embryonic stem cells," Cell (2003) 13(5): 643-55.
Chen et al., "Electrophysiological challenges of cell-based myocardial repair," Circulation (2009) 120:2496-2508.
Cheng et al., "Calcium sparks," Physiol Rev (2008) 88:1491-1545.
Chong et al., "Human embryonic-stem-cell-derived cardiomyocytes regenerate non-human primate hearts," Nature (2014) 510:273-277.
Cleemann et al., "Two-dimensional confocal images of organization, density, and gating of focal Ca2+ release sites in rat cardiac myocytes," Proc Natl Acad Sci USA (1998) 95:10984-10989.
Communication pursuant to Article 94(3) EPC for EP 10 853 137.7, dated May 6, 2015, 4 pages.
Cornell et al., "Activin-mediated mesoderm induction requires FGF," Development (1994) 120:453-462.
Domian et al., "Generation of functional ventricular heart muscle from mouse ventricular progenitor cells," Science (2009) 326:426-429.
Examination Report (Australia) for AU 2010355614, dated Sep. 13, 2013.
Fernandes, "Letter from the society president," J Biomol. Screening (1997) 2:1.
First Office Action for CN 201080067389.1, dated Jan. 26, 2014, 5 pages.
Fourth Amendment in Response to Examination Report for AU 2010355614, filed Jun. 5, 2015, 8 pages.
Fu et al., "Na+/Ca2+ exchanger is a determinant of excitation-contraction coupling in human embryonic stem cell-derived ventricular cardiomyocytes," Stem Cells Dev (2010) 19(6):773-782.
Gassanov et al., "Endothelin induces differentiation of ANP-EGFP expressing embryonic stem cells towards a pacemaker phenotype," FASEB Journal (2004) 18:1710-1712 (online version).
Gassanov et al., "Retinoid acid-induced effects on atrial and pacemaker cell differentiation and expression of cardiac ion channels," Differentiation (2008) 76:971-980.
Hao et al., "Dorsormorphin, a selective small molecule inhibitor of BMP signaling, promotes cardiomyogenesis in embryonic stem cells," PLoS One (2008) 3:e2904.
Hartung et al., "Toxicology for the twenty-first century," Nature (2009) 460(7252):208-212.
He et al., "Human embryonic stem cells develop into multiple types of cardiac myocytes: action potential characterization," Circ Res (2003) 93:32-39.
Hochgreb et al., "A caudorostral wave of RALDH2 conveys anteroposterior information to the cardiac field," Development (2003) 130:5363-5374.
Honda et al., "RXR agonist enhances the differentiation of cardiomyocytes derived from embryonic stem cells in serum-free conditions," Biochemical and Biophysical Research Communications (2005) 333:1334-1340.
Hong et al., "Development of efficient cardiac differentiation method of mouse embryonic stem cells," Key Engineering Materials (2007) 342-343:25-28.
International Preliminary Report on Patentability for PCT/CN2010/078645, dated Dec. 14, 2012, 7 pages.
International Search Report for PCT/CN2010/078645, dated Mar. 24, 2011, 4 pages.
International Search Report and Written Opinion (translation) for PCT/CN2013/079811, dated Oct. 24, 2013, 26 pages.
Itsykson et al., "Derivation of neural precursors from human embryonic stem cells in the presence of noggin," Mol Cell Neurosci (2005) 30:24-36.
Janzen et al., "High throughput screening as a discovery tool in the pharmaceutical industry," Lab Robotics Automation (1996) pp. 8261-8265.
Kattman et al., "Stage-Specific Optimization of Activin/Nodal and BMP Signaling Promotes Cardiac Differentiation of Mouse and Human Pluripotent Stem Cell Lines," Cell Stem Cell (2011) 8:228-240.
Keegan, "Retinoic acid signaling restricts the cardiac progenitor pool," Science (2005) 307:247-249.
Kehat et al., "Electromechanical integration of cardiomyocytes derived from human embryonic stem cells," Nat Biotechnol (2004) 22:1282-1289.
Kehat et al., "Human embryonic stem cells can differentiate into myocytes with structural and functional properties of cardiomyocytes," J Clin Invest (2001) 108(3):407-414.
Kennedy et al., "Retinoic acid enhances skeletal muscle progenitor formation and bypasses inhibition by bone morphogentic protein 4 but not dominant negative β-catenin," BMC Biology (2009) 7:67, 21 pages.
Korol et al., "A novel activity of the Dickkopf-1 amino terminal domain promotes axial and heart development independently of canonical Wnt inhibition," Dev Biol (2008) 324:131-138.
Laflamme et al., "Cardiomyocytes derived from human embryonic stem cells in pro-survival factors enhance function of infarcted rat hearts," Nat Biotechnol (2007) 25:1015-1024.
Lu et al., "Avian-induced pluripotent stem cells derived using human reprogramming factors," Stem Cells Dev. (2012) 21(3): 394-403.
Maltsev et al., "Embryonic stem cells differentiate in vitro into cardiomyocytes representing sinusnodal, atrial and ventricular cell types," Mech Dev (1993) 44:41-50.
Mandenius et al., "Cardiotoxicity testing using pluripotent stem cell-derived human cardiomyocytes and state-of-the-art bioanalytics: a review," J. Appl. Toxicol. (2011) 31:191-205.
Marvin et al., "Inhibition of Wnt activity induces heart formation from posterior mesoderm," Genes Dev (2001) 15:316-327.
Mummery et al. "Differentiation of human embryonic stem cells to cardiomyocytes: role of coculture with visceral endoderm-like cells." Circulation (2003) 107:2733-2740.
Niederreither et al., "Embryonic retinoic acid synthesis is essential for heart morphogenesis in the mouse," Development (2001) 128:1019-1031.

(56) References Cited

OTHER PUBLICATIONS

Nogrady, Medicinal Chemistry A Biochemical Approach, Oxford University Press, New York (1985) pp. 388-392.
Notice of Acceptance for AU 2010355614, dated Jun. 22, 2015, 2 pages.
Notification of Reasons for Rejection (translation) for JP 2013-514527, dated Jan. 27, 2015, 7 pages.
Notification of Decision of Rejection (with translation) for JP 2013-514527, dated Sep. 25, 2015, 15 pages.
Orts-Llorca et al., "Determination of heart polarity (atierio venous axis) in the chicken embryo," Raux Arch Entwick-lungsmechanik (1967) 113:17.
Pain et al., "Long-term in vitro culture and characterisation of avian embryonic stem cells with multiple morphogenetic potentialities," Development (1996) 122:2339-2348.
Patent Examination Report No. 2 for AU 2010355614, dated Sep. 16, 2014, 5 pages.
Patent Examination Report No. 3 for AU 2010355614, dated Feb. 17, 2015, 4 pages.
Patwardhan et al., "The rostro-caudal position of cardiac rnyocytes affect their fate," Dev Dyn (2000) 218:123-135.
Picht et al., "SparkMaster: automated calcium spark analysis with Image," Am J Physiol Cell Physiol (2007) 293:C1073-C1081.
Reppel et al., "Effect of cardioactive drugs on action potential generation and propagation in embryonic stem cell-derived cardiomyocytes," Cell Physiol Biochem (2007) 19:213-224.
Response to Communication pursuant to Rules 70(2) and 70a(2) EPC for EP 10 853 137.7, filed Aug. 5, 2014, 13 pages.
Response to First Office for CN 2010800673891, 14 pages.
Response to Second Office Action for CN 2010800673891, 76 pages.
Schneider et al., "Wnt antagonism initiates cardiogenesis in Xenopus laevis," Genes Dev (2001) 15:304-315.
Schulze et al., "BMS-189453, a novel retinoid receptor antagonist, is a potent testicular toxin," Toxicol Sci (2001) 59:297-308.
Second Amendment in Response to Examination Report for AU 2010355614, filed Aug. 26, 2014, 18 pages.
Second Office Action for CN 201080067389.1, dated Oct. 11, 2014, 10 pages.
Shimoji et al., "G-CSF promotes the proliferation of developing cardiornyocytes in vivo and in derivation from ESCs and iPSCs," Cell Stem Cell (2010) 6:227-237.
Shinzo (Heart's Selection 1) (2005) 37(14990-993 (English translation of introduction).
Shiraki et al., "Differentiation and characterization of embryonic stem cells into three germ layers," Biochemical and Biophysical Research Communications (2009) 381(4):694-699.
Supplementary European Search Report for EP 10853137.7, dated Jan. 14, 2014, 9 pages.
Supplementary European Search Report for EP 13823221.0, dated Mar. 4, 2016, 10 pages.
Takahashi et al., "Induction of pluripotent stem cells from adult human fibroblasts by defined factors," Cell (2007) 131:861-872.
Tesar et al., "New cell lines from mouse epiblast share defining features with human embryonic stem cells," Nature (2007) 448:196-199.
Third Amendment in Response to Examination Report No. 2 for AU 2010355614, filed Jan. 30, 2015, 12 pages.
Third Office Action for CN 201080067389.1, dated May 26, 2015, 10 pages.
Thomson et al., "Embryonic Stem Cell Lines Derived from Human Blastocysts," Science (1998) 282:1145-1147.
Tran et al., "Wnt3a-induced mesoderm formation and cardiomyogenesis in human embryonic stem cells," Stem Cells (2009) 27:1869-1878.
Ueno et al., "Biphasic role for Wnt/β-catenin signaling in cardiac specification in zebrafish and embryonic stem cells," PNAS (2007) 104(23):9685-9690.
Van Wijk et al., "Role of bone morphogentic proteins in cardiac differentiation", Cardiovascular Research (2007) 74:244-255.
Wobus et al., "Retinoic acid accelerates embryonic stem cell-derived cardiac differentiation and enhances development of ventricular cardiomyocytes," J Mol Cell Cardiol (1997) 29:1525-1539.
Woo et al., "Spatiotemporal characteristics of junctional and nonjunctional focal Ca2+ release in rat atrial myocytes," Circ Res (2003) 92:e1-11.
Written Opinion for PCT/CN2010/078645, dated Mar. 24, 2011, 18 pages.
Xavier-Neto et al., "A retinoic acid-inducible transgenic marker of sino-atrial development in the mouse heart," Development (1999) 126:2677-2687.
Xavier-Neto et al., "Retinoid signaling and cardiac anteroposterior segmentation," Genesis (2001) 31:97-104.
Xu et al., "Basic FGF and suppression of BMP signaling sustain undifferentiated proliferation of human ES cells," Nat Methods (2005) 2:185-190.
Xu et al., "BMP4 initiates human embryonic stem cell differentiation to trophoblast," Nat Biotechnol (2002) 20:1261-1264.
Xu, "Differentiation and enrichment of cardiomyocytes from human pluripotent stem cells," Journal of Molecular and Cellular Cardiology (2012) 52:1203-1212.
Xu et al., "Feeder-free growth of undifferentiated human embryonic stem cells," Nat Biotech (2001) 19:971-974.
Yanagita, "BMP antagonists: their roles in development and involvement in pathophysiology," Cytokine Growth Factor Rev (2005) 16:309-317.
Yang et al., "Human cardiovascular progenitor cells develop from a KDR+ embryonic-stem-cell-derived population," Nature (2008) 453:524-528.
Ying et al., "BMP induction of Id proteins suppresses differentiation and sustains embryonic stem cell self-renewal in collaboration with STAT3," Cell (2003) 115:281-292.
Yu et al., "Induced pluripotent stem cell lines derived from human somatic cells," Science (2007) 318:1917-1920.
Yuasa and Fukuda, "Cardiomyocyte Differentiation from Embryonic Stem Cells," Experimental Medicine (2008) 26(5)(extra edition):787-792 (with partial translation).
Yuasa et al., "Transient inhibition of BMP signaling by Noggin induces cardiomyocyte differentiation of mouse embryonic stem cells," Nat Biotechnol (2005) 23:607-611.
Yutzey et al., "Diversification of cardiornyogenic cell lineages in vitro," Dev Biol (1995) 170:531-541.
Zhang et al., "Direct differentiation of atrial and ventricular myocytes from human embryonic stem cells by alternating retinoid signals," Cell Research (2011) 21:579-587.
Zhang et al. "Short-term BMP-4 treatment initiates mesoderm induction in human embryonic stem cells." Blood (2008) 111(4):1933-1941.
Zhu et al., "Neuregulin/ErbB Signaling Regulates Cardiac Subtype Specification in Differentiating Human Embryonic Stem Cells," Circ Res (2010) 107(6):776-786.
Restriction Requirement for U.S. Appl. No. 13/703,608, dated Jun. 27, 2013, 9 pages.
Response to Restriction Requirement for U.S. Appl. No. 13/703,608, filed Jul. 26, 2013, 11 pages.
Office Action for U.S. Appl. No. 13/703,608, dated Sep. 13, 2013, 32 pages.
Response to Office Action for U.S. Appl. No. 13/703,608, filed Mar. 13, 2014, 20 pages.
Final Rejection for U.S. Appl. No. 13/703,608, dated Jul. 10, 2014, 19 pages.
Response to Final Rejection for U.S. Appl. No. 13/703,608, filed Sep. 9, 2014, 15 pages.
Advisory Action for U.S. Appl. No. 13/703,608, dated Oct. 1, 2014, 3 pages.
Request for Continued Examination for U.S. Appl. No. 13/703,608, filed Nov. 7, 2014, 3 pages.
Notice of Allowance for U.S. Appl. No. 13/703,608, dated Jun. 23, 2015, 11 pages.
Notice of Allowance for U.S. Appl. No. 13/703,608, dated Jul. 30, 2015, 4 pages.
Response to Notice of Allowance for U.S. Appl. No. 13/703,608, filed Sep. 23, 2015, 10 pages.

(56) References Cited

OTHER PUBLICATIONS

Response to Notice of Allowance for U.S. Appl. No. 13/703,608, filed Oct. 8, 2015, 4 pages.
Notice of Allowance for U.S. Appl. No. 13/703,608, dated Nov. 4, 2015, 4 pages.
Notice of Allowance for U.S. Appl. No. 13/703,608, dated Feb. 3, 2016, 2 pages.
Restriction Requirement for U.S. Appl. No. 14/417,101, dated Mar. 10, 2016, 9 pages.
Response to Restriction Requirement for U.S. Appl. No. 14/417,101, filed Apr. 20, 2016, 9 pages.
Fukuda et al., "Stem Cells as a Source of Regenerative Cardiomyocytes," Circ Res (2006) 98:1002-1013.
Hahn et al., "Pre-treatment of mesenchymal stem cells with a combination of growth factors enhances gap junction formation, cytoprotective effect on cardiomyocytes, and therapeutic efficacy for myocardial infarction," Journal of the American College of Cardiology (2008) 51:933-943.
Communication pursuant to Article 94(3) EPC for EP 13 823 221.0, dated Mar. 29, 2017, 5 pages.
Office Action for JP 2015-523397, dated Jun. 1, 2017, 6 pages (Including English translation).
Response to Examination Report for CA 2 802 526, dated Feb. 28, 2017, 3 pages.
Examination Report for CA 2 802 526, dated Jul. 6, 2017, 4 pages.
Response to Communication pursuant to Article 94(3) EPC for EP 10 853 137.7, dated Apr. 24, 2017, 13 pages.
First Examination Report for AU 2015230768, dated Jan. 20, 2017, 6 pages.
Response to Office Action for JP 2016-016994, dated Jun. 20, 2017, 7 pages.
Non-final Rejection for U.S. Appl. No. 14/417,101, dated May 5, 2016, 13 pages.
Response to Non-final Rejection for U.S. Appl. No. 14/417,101, dated Oct. 19, 2016, 21 pages.
Final Rejection for U.S. Appl. No. 14/417,101, dated Jan. 25, 2017, 15 pages.
Request for Continued Examination for U.S. Appl. No. 14/417,101, dated Jul. 25, 2017, 3 pages.
Bio, WNT pathway activator; Inhibits GSK3, available from https://www.stemcell.com/bio.html, accessed Oct. 19, 2016, 9 pages.
Communication pursuant to Article 94(3) EPC for EP 10 853 137.7, dated Oct. 13, 2016, 7 pages.
International Preliminary Report on Patentability for PCT/CN2013/079811, dated Jan. 27, 2015, 27 pages.
Müller et al., "Selection of ventricular-like cardiomyocytes from ES cells in vitro," The FASEB Journal (2000) 14:2540-2548.
Office Action for CA 2,802,526, dated Aug. 31, 2016, 4 pages.
Response to Examiner's Report for CA 2,802,526, dated Jan. 5, 2018, 5 pages.
Communication pursuant to Article 94(3) EPC for EP 10 853 137.7, dated Oct. 27, 2017, 4 pages.
Response to Examination Report for AU 2015230768, dated Nov. 29, 2017, 13 pages.
Notice of Acceptance for Patent Application for AU 2015230768, dated Nov. 30, 2017, 3 pages.
Notification of Reasons for Rejection for JP 2016-016994, dated Nov. 7, 2017, 10 pages (Including English translation).
Non-final Rejection for U.S. Appl. No. 14/417,101, dated Jan. 11, 2018, 30 pages.
Examination Report No. 1 for AU 2013295940, dated Jan. 22, 2018, 5 pages.
Response to Communication pursuant to Article 94(3) EPC for EP 13 823 221.0, dated Oct. 4, 2017, 12 pages.
Response to Office Action for JP 2015-523397, dated Dec. 1, 2017, 32 pages (Including English translation).
Notification of Reasons for Rejection for JP 2016-016994, dated Dec. 20, 2016, 22 pages (Including English Translation).
Naito et al., "Developmental stage-specific biphasic roles of Wnt/β-catenin signaling in cardiomyogenesis and hematopoiesis," PNAS (2006) 103(52):19812-19817.
Cao et al. "Transcriptional and functional profiling of human embryonic stem cell-derived cardiomyocytes", PloS One, 2008, 3(10), e3474.
Lee et al. "Human Pluripotent Stem Cell-Derived Atrial and Ventricular Cardiomyocytes Develop from Distinct Mesoderm Populations", Cell Stem, dated Aug. 3, 2017, Cell 21, pp. 179-194 http://dx.doi.org/10.1016/j.stem.2017.07.003.
Rosenthal and Xavier-Neto, "From the bottom of the heart: anteroposterior decisions in cardiac muscle differentiation", Curr Opin Cell Bio. dated Dec. 2000, 12(6), pp: 742-746 (Year: 2002).
Hen et al. "Pretreatment of Measenchymal Stem Cells With a Combination of Growth Factors Enhances Gap Junction Formation, Cytoprotective Effect on Cardiomyocytes, and Therapeutic Efficacy for Myocardial Infarction", Journal of the American College of Cardiology, 2008, vol. 51, No. 9, pp. 933-943.
United States Patent and Trademark Office, Office communication concerning U.S. Appl. No. 14/417,101 and proceeding, dated Jan. 11, 2018, 30 pages.
United States Patent and Trademark Office, Response to Office Action for U.S. Appl. No. 14/417,101, dated Jul. 1, 2018, 27 pages.
Australian Government IP Australia, First Examination report for standard paten application 2013295940, dated Jan. 22, 2018, 5 pages.
European Patent Office, Office Action for Communication pursuant to Article 94(3) EPC for EP application 13823221.0-1120, dated Mar. 16, 2018, 4 pages.
European Patent Office, Office Action Responsive to the Communication pursuant to Article 94(3) EPC for EP application 13823221.0, dated Jul. 26, 2018, 10 pages.
Japan Patent Office, Office Action, Notice of reason for rejection for JP application 2015-523397, dated Feb. 13, 2018, 4 pages (including English translation additional 6 pages).
Canadian Intellectual Property Office, Office action for patent application 2,802,526 (PCT/CN2010078645), dated May 8, 2018, 4 pages.
European Patent Office, Office action of Communication pursuant to Article 94(3) EPC for patent application 10853137.7-1120, dated Jul. 25, 2018, 3 pages.
Japan Patent Office, Response to 2nd Office action (dated Feb. 13, 2018) for patent application 2015-523397, dated Aug. 24, 2018, 11 pages (with additional 10 pages of English translation).
Japan Patent Office, Notice of Allowance for patent application 2015-523397, dated Aug. 31, 2018, 3 pages.
Japan Patent Office, Notice of Allowance for patent application 2016-016994, dated Sep. 21, 2018, 3 pages.
United States Patent and Trademark Office, Office communication for U.S. Appl. No. 14/417,101, dated Oct. 16, 2018, 31 pages.
Response to Office Action for European patent application EP10853137.7, dated Jan. 29, 2019, 52 pages.
Communication pursuant to Article 94(3) EPC for European patent application EP10853137.7, dated Jul.. 24, 2019, 3 pages.
Division Patented Claims for Japanese patent application JP2016-16994, dated Nov. 21, 2018, 3 pages.
Japanese Patent JP 6427126 B2, dated Nov. 21, 2018, 26 pages.
Final Office Action for U.S. Appl. No. 14/417,101, dated Oct. 16, 2018, 31 pages.
Exhibit 1 in re Sussman,141 F.2d 267 (C.C.P.A. 1944) • 60 U.S.P.Q. 538, Decided Feb. 7, 1944, 7 pages.
Exhibit 2 Par Pharmaceutical v. TWI Pharmaceutiacals, Inc., 773 F.3d 1186 (2014), 8 pages.
Request of Continue Examination for U.S. Appl. No. 14/417,101, dated Apr. 15, 2019, 3 pages.
Response to Final Office Action for U.S. Appl. No. 14/417,101, dated Apr. 15, 2019, 21 pages.
Non-Final Office Action for U.S. Appl. No. 14/417,101, dated Oct. 3, 2019, 30 pages.
Response to Examination Report for Australian patent application AU2013295940, dated Dec. 13, 2018, 40 pages.
Examination Report No. 2 for Australian patent application AU2013295940, dated Jan. 8, 2019, 3 pages.

(56) References Cited

OTHER PUBLICATIONS

Claims (Amendment #2) for Australian patent application AU2013295940, dated Jan. 15, 2019, 5 pages.
Final Response to Examination Report for Australian patent application AU2013295940, dated Jan. 15, 2019, 34 pages.
Claims as Accepted for Australian patent application AU2013295940, dated Jan. 21, 2019, 5 pages.
Notice of acceptance and Bibliographic Attachment for Australian patent application AU2013295940, dated Jan. 21, 2019, 3 pages.
Notice of grant for patent for Australian patent application AU2013295940, dated May 16, 2019, 2 pages.
Published specification for Australian patent application AU2013295940, dated May 17, 2019, 49 pages.
Notice of Abandonment for Canadian patent application CA2,802,526, dated Dec. 20, 2018, 1 page.
Office Action for Canadian patent application CA2,886,396, dated Mar. 22, 2019, 4 pages.
Amended claims for Canadian patent application CA2,886,396, dated Sep. 19, 2019, 8 pages.
Response Office Action for Canadian patent application CA2,886,396, dated Sep. 19, 2019, 33 pages.
Amended Claims for European patent application EP13 823 221.0, dated Jul. 25, 2018, 3 pages.
Response to the communication pursuant to Article 94(3) EPC for European patent application EP13 823 221.0, dated Mar. 6, 2019, 8 pages.
Communication pursuant to Article 94(3) EPC for European patent application EP13 823 221.0, dated Sep. 9, 2019, 4 pages.

* cited by examiner

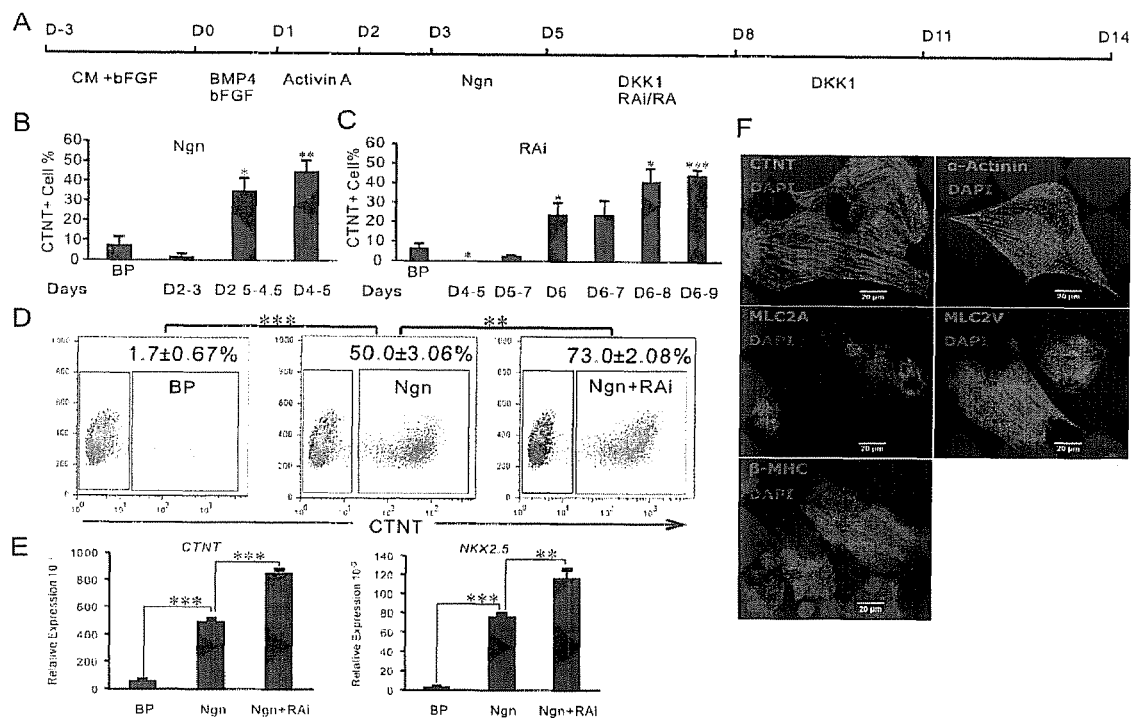
Figure 1 Noggin (Ngn) and RA inhibition promote hESC cardiac differentiation.

Figure 2. Morphologies and beating rates of differentiated cardiomyocytes.
A
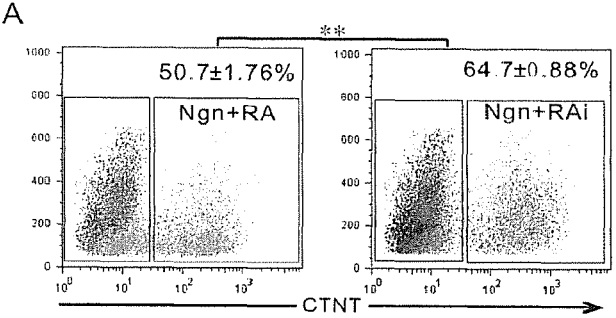
B
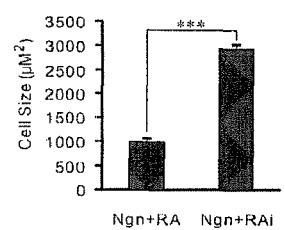
C
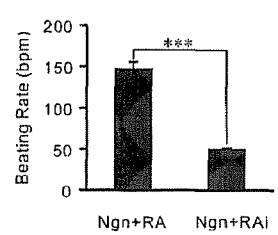
D
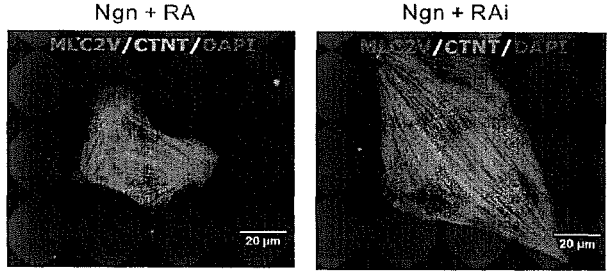

Figure 3 Characterization of hESC-derived cardiomyocytes, induced by Ngn+RA and Ngn+RAi.
A
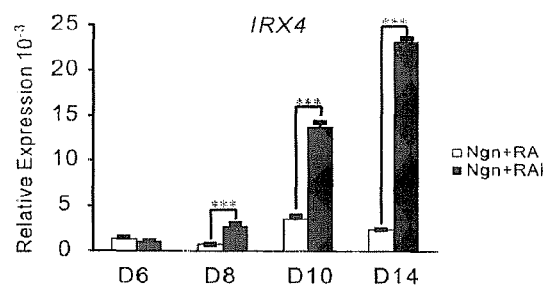
B
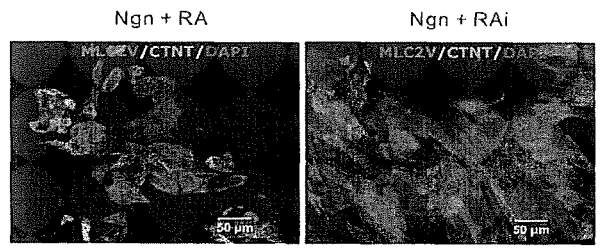
C
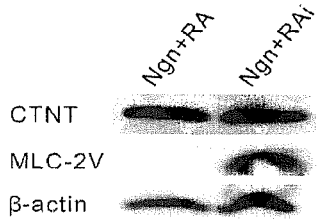

Figure 4 AP morphologies and Ca2+ release properties of cardiomyocytes induced by Ngn+RA and Ngn+RAi.
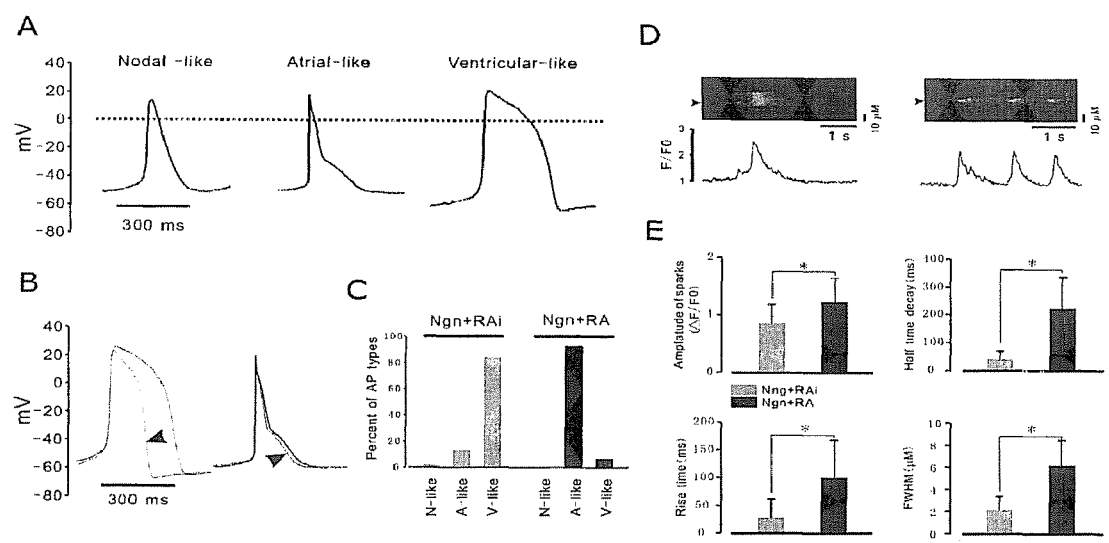

Figure 5 MLC-2v expression in different retinoid treated cultures.
A
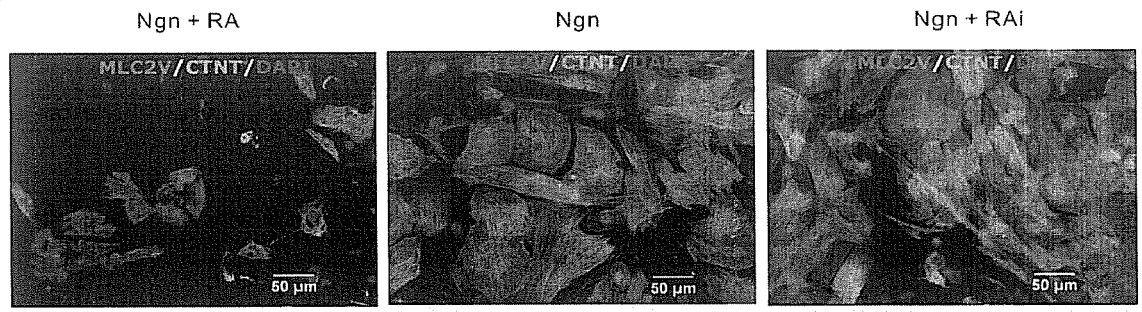
B
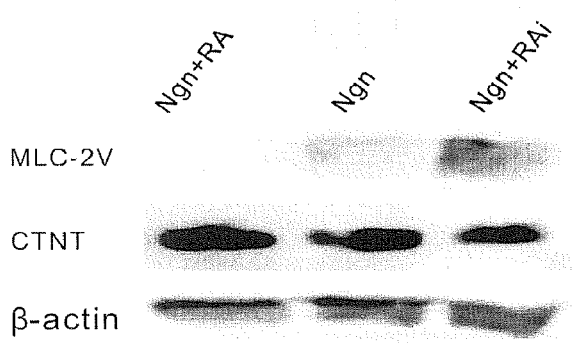
Figure 6 Cardiac gene expression in differently treated cultures.
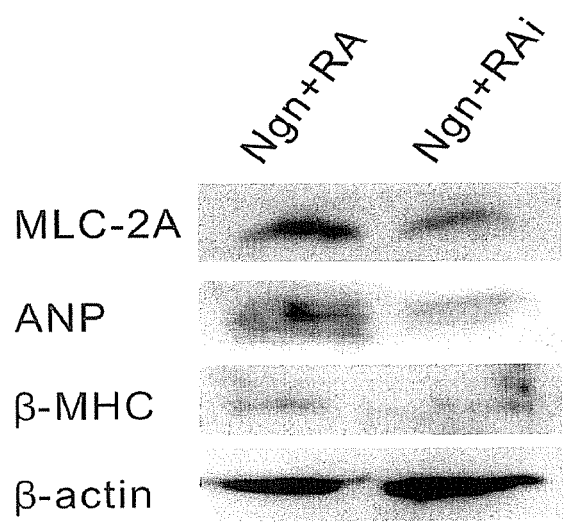

SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Forward primer_gene NXK2.5

<400> SEQUENCE: 1
acctcaacag ctccctgact ct                                              22

<210> SEQ ID NO 2

```
<211> LENGTH: 23
<212> TYPE: DNA
<213> ORGANISM: Artificial Sequence
<220> FEATURE:
<223> OTHER INFORMATION: Reverse primer_gene NXK2.5

<400> SEQUENCE: 2
ataatcgccg ccacaaactc tcc                                              23

<210> SEQ ID NO 3
<211> LENGTH: 24
<212> TYPE: DNA
<213> ORGANISM: Artificial Sequence
<220> FEATURE:
<223> OTHER INFORMATION: Forward primer_gene CTNT

<400> SEQUENCE: 3
ttcaccaaag atctgctcct cgct                                             24

<210> SEQ ID NO 4
<211> LENGTH: 26
<212> TYPE: DNA
<213> ORGANISM: Artificial Sequence
<220> FEATURE:
<223> OTHER INFORMATION: Reverse primer_gene CTNT

<400> SEQUENCE: 4
ttattactgg tgtggagtgg gtgtgg                                           26

<210> SEQ ID NO 5
<211> LENGTH: 21
<212> TYPE: DNA
<213> ORGANISM: Artificial Sequence
<220> FEATURE:
<223> OTHER INFORMATION: Forward primer_gene IRX4

<400> SEQUENCE: 5
ttccgttctg aagcbgtggt c                                                21

<210> SEQ ID NO 6
<211> LENGTH: 22
<212> TYPE: DNA
<213> ORGANISM: Artificial Sequence
<220> FEATURE:
<223> OTHER INFORMATION: Reverse primer_gene IRX4

<400> SEQUENCE: 6
tgaagcaggc aattattggt gt                                               22

<210> SEQ ID NO 7
<211> LENGTH: 24
<212> TYPE: DNA
<213> ORGANISM: Artificial Sequence
<220> FEATURE:
<223> OTHER INFORMATION: Forward primer_gene GAPDH

<400> SEQUENCE: 7
gaaatcccat caccatcttc cagg                                             24

<210> SEQ ID NO 8
<211> LENGTH: 20
<212> TYPE: DNA
<213> ORGANISM: Artificial Sequence
```

```
<220> FEATURE:
<223> OTHER INFORMATION: Reverse primer_gene GAPDH

<400> SEQUENCE: 8
gagccccagc cttctccatg                                          20
```

METHODS AND COMPOSITIONS FOR PREPARING CARDIOMYOCYTES FROM STEM CELLS AND USES THEREOF

CROSS-REFERENCE TO RELATED APPLICATIONS

This application is a continuation of U.S. patent application Ser. No. 13/703,608, filed Feb. 28, 2013, which is a national phase of PCT application PCT/CN2010/078645 having an international filing date of Nov. 11, 2010, entitled "Methods and Compositions for Preparing Cardiomyocytes From Stem Cells and Uses Thereof," which claims priority to Chinese Application No. 201010207603.0 filed Jun. 13, 2010, entitled "Methods for Efficiently Differentiating Stem Cells into Atrial and Ventricular Cardiomyocytes." The contents of these applications are incorporated herein by this reference in their entireties.

TECHNICAL FIELD

The present invention relates to novel compositions and methods for enhancing cardiac differentiation efficiency of stem cells and for promoting atrial and ventricular cardiomyocytes formation from stem cells, the atrial and ventricular cardiomyocytes formed from the stem cells, and the uses of the cardiomyocytes, e.g., for cardiac injury repair and screening for new therapeutics for treating cardiac injuries.

BACKGROUND OF THE INVENTION

Using current technologies, embryonic atrial-, ventricular- and nodal-like cardiomyocytes can be differentiated non-specifically from hESCs[6-9]. Swine transplantation studies show that implanted hESC derived cardiomyocytes have pace making activities, a potential cause of ventricular arrhythmias[10]. The application of hESCs in myocardial repair is hampered by this cardiac subtype heterogeneity of hESC-derived cardiomyocytes[1]. To direct differentiation of hESCs into a desired cardiac subtype, the mechanisms of cardiac subtype specification have to be uncovered. Although several growth factors, such as activin A, bone morphogenetic protein 4 (BMP4), wnt-3a, basic fibroblast growth factor (bFGF) and dickkopf homolog 1 (DKK1), have been identified to promote cardiogenesis, and are used in several hESC cardiac differentiation protocols[7,8,11], there is no evidence up to date showing that these or other growth factors regulate the cardiac subtype specification during hESC differentiation. Identifying the key regulators of cardiac subtype specification is critical for reducing the heterogeneity of hESC-derived cardiomyocyte population which will be important for its later use in regenerative medicine or as drug test systems[6,12].

Bone morphogenetic protein (BMP) signaling is tightly controlled during mesoderm and heart development. In mouse embryos, the BMP antagonist Noggin is transiently but strongly expressed in the cardiac crescent at embryo day E7.5 to E8.0[13]. Dkk1, a potent inducer of heart development[8,14,15], synergizes with BMP antagonism to specify heart tissue in non-cardiogenic mesoderm from Xenopus embryos[16]. It has been shown that long term treatment of hESCs with BMP4 induces trophoblast-like cell differentiation[17], while short term treatment initiates mesoderm formation[18]. Together, these results suggest that inhibiting BMP signaling after mesoderm formation facilitates cardiac development.

Retinoic acid (RA) signaling not only restricts the cardiac progenitor pool, and exposure of the anterior lateral plate mesoderm of zebrafish embryos to the RA antagonist BMS-189453 causes uncommitted lateral mesodermal cells to become myocardial progenitors[19], but also regulates anterior-posterior polarization of the heart[20]. Chicken transplantation studies have revealed that the cardiogenic mesoderm from HH stages 4-6, originally fated to be atria, is competent to develop into functional ventricles and vice versa[21,22]. RA treatment of HH stage 4 cardiogenic tissue activates the expression of the atrium-specific gene AMHC1 in anterior progenitors fated to develop into out-flow track tissues[23]. Furthermore, in both mouse and chicken embryos, inhibition of RA signaling within critical periods produces embryos with oversized ventricles and smaller or missing atria, and exogenous addition of RA results in reverted phenotypes[5,24]. Furthermore, studies with mouse embryonic stem cells indicated retinoic acid promotes the expression of atrial related genes[25].

DISCLOSURE OF THE INVENTION

In one aspect, the present disclosure provides a method for enhancing cardiac differentiation efficiency of a stem cell, which method comprises inhibiting BMP signaling after the initiation of differentiation, or cardiac differentiation, of the stem cell. In one specific embodiment, the present disclosure provides a method for enhancing cardiac differentiation efficiency of a stem cell, which method comprises contacting a stem cell that has differentiated to form mesoderm with a bone morphogenetic protein (BMP) antagonist, whereby the cardiac differentiation efficiency of the stem cell contacted with the BMP antagonist is higher than the cardiac differentiation efficiency of the stem cell not contacted with the BMP antagonist. The cardiomyocytes produced by the above method are also provided. A composition comprising a stem cell that has differentiated to form mesoderm and treated with an exogenous BMP antagonist is further provided.

In another aspect, the present disclosure provides a method for promoting ventricular cardiomyocyte formation from a stem cell, which method comprises inhibiting retinoic acid signaling pathway in a stem cell that has differentiated to form mesoderm. Ventricular cardiomyocytes produced by the above method are also provided. A composition comprising a stem cell that has differentiated to form mesoderm and treated with an exogenous agent that inhibits retinoic acid signaling pathway in the stem cell is further provided.

In still another aspect, the present disclosure provides a method for promoting atrial cardiomyocyte formation from a stem cell, which method comprises stimulating or not inhibiting retinoic acid signaling pathway in a stem cell that has differentiated to form mesoderm. Atrial cardiomyocytes produced by the above method are also provided. A composition comprising a stem cell that has differentiated to form mesoderm and treated with an exogenous agent that stimulates retinoic acid signaling pathway in the stem cell is further provided.

In yet another aspect, the present disclosure provides a method for generating a ventricular cardiomyocyte from a stem cell, which method comprises: 1) contacting a stem cell with an agent, e.g., bFGF and BMP 4, to initiate stem cell differentiation; 2) contacting the stem cell treated by the agent, e.g., bFGF and BMP 4, with another agent, e.g., activin A, to form mesoderm; 3) contacting the stem cell that has differentiated to form mesoderm with a BMP antagonist such as Noggin, to enhance cardiac differentiation efficiency of the stem cell; 4) inhibiting retinoic acid signaling pathway in the stem cell treated by BMP antagonist, e.g., Noggin, to promote ventricular cardiomyocyte formation; and 5) contacting the stem cell treated by BMP antagonist, e.g., Noggin, with a wnt inhibitor, such as DKK1, to differentiate the stem cell into a ventricular cardiomyocyte. Ventricular cardiomyocytes produced by the above method are also provided.

In yet another aspect, the present disclosure provides a method for generating a ventricular cardiomyocyte from a stem cell, which method comprises: 1) contacting a stem cell with bFGF and BMP 4; 2) contacting the stem cell treated by bFGF and BMP 4 with activin A; 3) contacting the stem cell that has been treated by activin A with Noggin; 4) inhibiting retinoic acid signaling pathway in the stem cell treated by Noggin; and 5) contacting the stem cell treated by Noggin with DKK1. Ventricular cardiomyocytes produced by the above method are also provided.

In yet another aspect, the present disclosure provides a method for generating an atrial cardiomyocyte from a stem cell, which method comprises: 1) contacting a stem cell with an agent, e.g., bFGF and BMP 4, to initiate stem cell differentiation; 2) contacting the stem cell treated by the agent, e.g., bFGF and BMP 4, with another agent, e.g., activin A, to form mesoderm; 3) contacting the stem cell that has differentiated to form mesoderm with a BMP antagonist, such as Noggin, to enhance cardiac differentiation efficiency of the stem cell; 4) stimulating or not inhibiting retinoic acid signaling pathway in the stem cell treated by Noggin to promote atrial cardiomyocyte formation; and 5) contacting the stem cell treated by Noggin with DKK1 to differentiate the stem cell into an atrial cardiomyocyte. Atrial cardiomyocytes produced by the above method are also provided.

In yet another aspect, the present disclosure provides a method for generating an atrial cardiomyocyte from a stem cell, which method comprises: 1) contacting a stem cell with bFGF and BMP 4; 2) contacting the stem cell treated by bFGF and BMP 4 with activin A; 3) contacting the stem cell that has been treated by activin A with Noggin; 4) stimulating or not inhibiting retinoic acid signaling pathway in the stem cell treated by Noggin; and 5) contacting the stem cell treated by Noggin with DKK1. Atrial cardiomyocytes produced by the above method are also provided.

In yet another aspect, the present disclosure provides a pharmaceutical composition for treating a cardiac injury or disorder, which pharmaceutical composition comprises an effective amount of the cardiomyocytes produced by the above methods, and optionally a pharmaceutically acceptable carrier or excipient.

In yet another aspect, the present disclosure provides a method for treating a cardiac injury or disorder in a subject, e.g., a human, which method comprises administering, to a subject to which such treatment is needed or desirable, an effective amount of the above pharmaceutical composition.

In yet another aspect, the present disclosure provides a method for identifying a modulator of a cardiomyocyte, which method comprises: 1) contacting a cardiomyocyte produced by the above methods with a test substance and measuring the effect of the test substance on a property of the cardiomyocyte; 2) measuring the property of the cardiomyocyte not contacted with the test substance; whereby the property of the cardiomyocyte contacted with the test substance is different from that of the cardiomyocyte not contacted with the test substance identifies the test substance as a modulator, e.g., a stimulator or inhibitor, of the property of the cardiomyocyte.

BRIEF DESCRIPTION OF THE DRAWINGS

FIG. 1 shows that Noggin (Ngn) and RA inhibition promote hESC cardiac differentiation. (A) An outline of the protocol used for the differentiation of human ESCs to cardiac lineages. (B) Frequencies of CTNT+ cells at day 14; cardiac-induced cultures with addition of Ngn at the time intervals indicated; the basic protocol (BP) was used as a control. (C) Frequencies of CTNT+ cells in day 14 cardiac-induced cultures with addition of the RA inhibitor, RAi at the time intervals indicated; BP was used as a control. (D) Flow cytometry analysis of CTNT+ cells in cultures with BP as a control; BP cultures with Ngn added at days 4 and 5, and BP cultures with Ngn added at days 4 and 5, and RAi added from day 6 to day 8 (Ngn+RAi). (E) Quantitative RT-PCR gene expression analysis of day 14 BP, Ngn-treated, and Ngn+RAi-treated cultures, as indicated in (D) The average expression, normalized to GADPH, is shown. (F) Immunostaining analysis of cardiac-induced cultures. Where shown, bars represent the standard error of the mean of three independent experiments. CM, conditioned medium. P compared with the BP control or otherwise indicated, *P<0.05, P<0.005, *P<0.0005.

FIG. 2 shows morphologies and beating rates of differentiated cardiomyocytes. (A) Flow cytometry analysis of CTNT+ cells from day 14 cultures, differentiated with the BP, plus treatments with Ngn at days 4 and 5, and RA (Ngn+RA) or RAi (Ngn+RAi.) treatment from days 6 to 8. (B) Statistics of the size of single cardiomyocytes from 60 day-old cultures treated with Ngn+RA (n=35) and Ngn+RAi (n=31), measured with ImageJ software. (C) Statistics of the beating rates (beat/minute) of 60 day-old differentiated cultures (n=4). (D) Immunostaining of single cells from 60 day-old differentiated cultures.

FIG. 3 shows characterization of hESC-derived cardiomyocytes, induced by Ngn+RA and Ngn+RAi. (A) Quantitative RT-PCR analysis of the kinetics of irx4 gene expression in Ngn+RA and Ngn+RAi cultures. The average expression, normalized to GAPDH, is shown. Where shown, bars represent the standard error of the mean of three independent experiments. ***P<0.0005. (B) Immunostaining of 60 day-old Ngn+RA and Ngn+RAi induced cultures, demonstrated MLC-2V expression in the majority of CTNT+ cells of Ngn+RAi treated cultures but not in those of Ngn+RA treated cultures. (C) Western blotting of 60 day-old Ngn+RA and Ngn+RAi treated cultures, indicated that even though CTNT is evenly expressed in both cultures, MLC-2V is strongly expressed in Ngn+RAi-treated cultures but not in Ngn+RA treated cultures.

FIG. 4 shows AP morphologies and Ca2+ release properties of cardiomyocytes induced by Ngn+RA and Ngn+RAi. (A) Three major types of APs were observed in hESC-derived cardiomyoctes: nodal-like, atrial-like, and ventricular-like. The duration of the ventricular-like APs was greatly reduced by application of nifedipine (B, left); No significant effect of nifedipine on atrial-like AP duration was observed (B, right). (C) the percentages of AP types recorded from Ngn+RAi and Ngn+RA cultures are indicated. (D) Typical $Ca^{2+}$ images recorded from cardiomyocytes in Ngn+RA cultures (left) and Ngn+RAi cultures (right). Fluorescence profiles (bottom) were taken from the images (at positions indicated by arrows). The properties of typical $Ca^{2+}$ release events recorded from cardiomyocytes in Ngn+RA and Ngn+RAi-treated cultures are summarized in e (98 sparks from 18 cells in Ngn+RA-treated cultures, and 348 sparks from 14 cells in Ngn+RAi-treated cultures were measured). *P<0.05 compared with Ngn+RAi cultures. All cells used in electrophysiological studies were 60 to 90 days old. N-like, nodal like AP; A-like, atrial like AP; V-like, ventricular-like AP.

FIG. 5 shows MLC-2v expression in different retinoid treated cultures. (A) MLC-2v and cTNT double staining for 60 day old cultures treated with Noggin+RA, Noggin alone and Noggin+RAi. (B) Western blots for MLC-2v, cTNT and β-actin with 60 day old cultures treated with Noggin+RA, Noggin alone and Noggin+RAi.

FIG. 6 shows cardiac gene expression in different treated cultures. Western blots for MLC-2a, ANF, β-MHC and β-actin with 60 day old cultures treated with Noggin+RA, Noggin alone and Noggin+RAi.

DETAILED DESCRIPTION OF THE INVENTION

A. Definitions

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "mammal" refers to any of the mammalian class of species. Frequently, the term "mammal," as used herein, refers to humans, human subjects or human patients.

As used herein, "an effective amount of a compound for treating a particular disease" is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, "treatment" means any manner in which the symptoms of a condition, disorder or disease are ameliorated or otherwise beneficially altered. Treatment also encompasses any pharmaceutical use of the compositions herein.

As used herein, "amelioration" of the symptoms of a particular disorder by administration of a particular pharmaceutical composition refers to any lessening, whether permanent or temporary, lasting or transient that can be attributed to or associated with administration of the composition.

As used herein, "production by recombinant means" refers to production methods that use recombinant nucleic acid methods that rely on well known methods of molecular biology for expressing proteins encoded by cloned nucleic acids.

As used herein, the term "subject" is not limited to a specific species or sample type. For example, the term "subject" may refer to a patient, and frequently a human patient. However, this term is not limited to humans and thus encompasses a variety of mammalian species.

As used herein, "pharmaceutically acceptable salts, esters or other derivatives" include any salts, esters or derivatives that may be readily prepared by those of skill in this art using known methods for such derivatization and that produce compounds that may be administered to animals or humans without substantial toxic effects and that either are pharmaceutically active or are prodrugs.

As used herein, a "prodrug" is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

As used herein, "test substance (or candidate compound)" refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on PTH antagonist is determined by the disclosed and/or claimed methods herein.

As used herein, high-throughput screening (HTS) refers to processes that test a large number of samples, such as samples of diverse chemical structures against disease targets to identify "hits" (see, e.g., Broach, et al., High throughput screening for drug discovery, *Nature*, 384:14-16 (1996); Janzen, et al., High throughput screening as a discovery tool in the pharmaceutical industry, *Lab Robotics Automation:* 8261-265 (1996); Fernandes, P. B., Letter from the society president, *J. Biomol. Screening*, 2:1 (1997); Burbaum, et al., New technologies for high-throughput screening, *Curr. Opin. Chem. Biol.*, 1:72-78 (1997)). HTS operations are highly automated and computerized to handle sample preparation, assay procedures and the subsequent processing of large volumes of data.

B. Methods and Compositions for Enhancing Cardiac Differentiation Efficiency of Stem Cells and Cardiomyocyte Produced Thereof In one aspect, the present disclosure provides a method for enhancing cardiac differentiation efficiency of a stem cell, which method comprises contacting a stem cell that has differentiated to form mesoderm with a bone morphogenetic protein (BMP) antagonist, whereby the cardiac differentiation efficiency of the stem cell contacted with the BMP antagonist is higher than the cardiac differentiation efficiency of the stem cell not contacted with the BMP antagonist. The cardiomyocytes produced by the above method are also provided. A composition comprising a stem cell that has differentiated to form mesoderm and treated with an exogenous BMP antagonist is further provided.

The present method can be used to enhance cardiac differentiation efficiency of any suitable stem cell. For example, the present method can be used to enhancing cardiac differentiation efficiency of a totipotent, pluripotent, multipotent, oligopotent or unipotent stem cell. In another example, the present method can be used to enhancing cardiac differentiation efficiency of an embryonic stem cell, an induced pluripotent stem cell, a fetal stem cell or an adult stem cell. In still another example, the present method can be used to enhancing cardiac differentiation efficiency of a mammalian stem cell such as a human stem cell. In still another example, the present method can be used to enhancing cardiac differentiation efficiency of a human embryonic stem cell or a human induced pluripotent stem cell.

The stem cells can be obtained, prepared and/or maintained by any suitable methods. For example, mouse ES cells can grow on a layer of gelatin and require the presence of Leukemia Inhibitory Factor (LIF). Human ES cells can grow on a feeder layer of mouse embryonic fibroblasts (MEFs) and may require the presence of basic Fibroblast Growth Factor (bFGF or FGF-2) (See e.g., Chambers I, Colby D, Robertson M, et al. (2003). "Functional expression cloning of Nanog, a pluripotency sustaining factor in embryonic stem cells". *Cell* 113 (5): 643-55).

A stem cell, e.g., a human embryonic stem cell, is often defined by the presence of several transcription factors and cell surface proteins. For example, the transcription factors Oct-4, Nanog, and Sox2 form the core regulatory network that ensures the suppression of genes that lead to differentiation and the maintenance of pluripotency. The cell surface antigens commonly used to identify hES cells are the glycolipids SSEA3 and SSEA4 and the keratan sulfate antigens Tra-1-60 and Tra-1-81.

Induced pluripotent stem cells, commonly abbreviated as iPS cells or iPSCs, are a type of pluripotent stem cell artificially derived from a non-pluripotent cell, typically an adult somatic cell, by inducing a "forced" expression of specific genes. Various genes, or a combination thereof, can be used to induce iPS cells from adult somatic cells. For example, Oct-3/4 and certain members of the Sox gene family (Sox1, Sox2, Sox3, and Sox15) can be used to induce iPS cells from adult somatic cells. Additional genes, including certain members of the Klf family (Klf1, Klf2, Klf4, and Klf5), the Myc family (C-myc, L-myc, and N-myc), Nanog, and LIN28, can be used to increase the induction efficiency. The various genes or its encoded proteins can be delivered into the adult somatic cells by any suitable methods. For example, various genes can be delivered into the adult somatic cell by a viral transfection system, such as a retroviral system, a lentiviral system, or an adenoviral system, or a plasmid without any virus transfection system. Alternatively, proteins encoded by the genes can be delivered into the adult somatic cells directly, e.g., by a repeated treatment of the cells with certain proteins channeled into the cells via poly-arginine anchors.

The stem cell can be induced to differentiate to form mesoderm by any suitable treatment or agent. In one example, the stem cell has differentiated to form mesoderm by contacting an undifferentiated stem cell with basic fibroblast growth factor (bFGF), BMP 4 and/or activin A. In another example, the stem cell has differentiated to form mesoderm by contacting an undifferentiated stem cell with basic fibroblast growth factor (bFGF), BMP 4 and activin A. The stem cell can be treated with bFGF, BMP 4 and activin A in any suitable order. For example, the stem cell can be differentiated to form mesoderm by contacting an undifferentiated stem cell with basic fibroblast growth factor (bFGF) and BMP 4 before the stem cell is contacted with activin A. In another example, the stem cell can be differentiated to form mesoderm by contacting an undifferentiated stem cell with wnt-3a (Tran, T. H. et al. Wnt3a-induced mesoderm formation and cardiomyogenesis in human embryonic stem cells. *Stem Cells* 27, 1869-1878 (2009)), or a small molecule which acts or functions like wnt-3a, such as Bio or CHIR99021.

Any suitable BMP antagonist can be used in the present methods to enhance cardiac differentiation efficiency of a stem cell. For example, a BMP 4 antagonist can be used. In another example, the BMP antagonist is Noggin. In still another example, the BMP antagonist is Chordin, Tsg, a member of DAN family (Yanagita, M. BMP antagonists: their roles in development and involvement in pathophysiology. *Cytokine Growth Factor Rev* 16, 309-317, (2005)), BMP soluble receptors, such as BMPR1A and BMPR1B, or a small molecule which acts or functions like BMP antagonist, such as Dorsomorphin (Hao, J. et al. Dorsomorphin, a selective small molecule inhibitor of BMP signaling, promotes cardiomyogenesis in embryonic stem cells. *PLoS One* 3, e2904 (2008)).

The present methods can further comprise inhibiting retinoic acid signaling pathway in the stem cell. The retinoic acid signaling pathway in the stem cell can be inhibited by any suitable treatment or agent. In one example, the retinoic acid signaling pathway is inhibited by contacting the stem cell with a retinoic acid antagonist, a retinoic acid receptor antagonist or a retinoic X receptor antagonist. In another example, the retinoic acid signaling pathway is inhibited by contacting the stem cell with a pan-retinoic acid receptor antagonist, e.g., BMS-189453. In still another example, the retinoic acid signaling pathway is inhibited by contacting the stem cell with BMS-453, AGN194310, ANG193109, Ro41-5253, SR11335, 9-cis-retinoic acid, or a small molecule that inhibits retinoic acid synthesis, such as disulfiram and citral. In yet another example, the retinoic acid signaling pathway is inhibited by reducing or depleting vitamin A in the culture medium for the stem cell.

The present methods can be used to enhance cardiac differentiation efficiency of a stem cell to a suitable degree. In one example, the cardiac differentiation efficiency of the stem cell contacted with the BMP antagonist is at least about 30% higher than the cardiac differentiation efficiency of the stem cell not contacted with the BMP antagonist. In specific embodiments, the cardiac differentiation efficiency of the stem cell contacted with the BMP antagonist is at least about 40%, 50%, 60%, 70%, 80%, 90%, 100%, 2-fold, 3-fold, 4-fold, 5-fold, 6-fold, 7-fold, 8-fold, 9-fold, 10-fold, or higher than the cardiac differentiation efficiency of the stem cell not contacted with the BMP antagonist.

In one specific example, the stem cell is a human embryonic stem cell or a human induced pluripotent stem cell, the BMP antagonist is Noggin and the cardiac differentiation efficiency of the stem cell contacted with the BMP antagonist is about 10%, 20%, 30%, 40%, 50%, 60%, 70% or 80%. In another specific example, the stem cell is a human embryonic stem cell or a human induced pluripotent stem cell, the BMP antagonist is Noggin and the cardiac differentiation efficiency of the stem cell contacted with the BMP antagonist is about 60%, 70%, 80%, 90%, 95% or 100%.

The present methods can further comprise contacting the stem cell with a wnt inhibitor to differentiate the stem cell into a cardiomyocyte. Any suitable wnt inhibitor can be used. In one example, the wnt inhibitor is dickkopf homolog 1 (DKK1).

A cardiomyocyte produced by the above methods is also provided.

A composition comprising a stem cell that has differentiated to form mesoderm and treated with an exogenous BMP antagonist is further provided.

C. Methods and Compositions for Promoting Ventricular Cardiomyocyte Formation and Ventricular Cardiomyocyte Produced Thereof In another aspect, the present disclosure provides a method for promoting ventricular cardiomyocyte formation from a stem cell, which method comprises inhibiting retinoic acid signaling pathway in a stem cell that has differentiated to form mesoderm.

The present methods can be used to promote ventricular cardiomyocyte formation from any suitable stem cell. In one example, the present methods can be used to promote ventricular cardiomyocyte formation from a totipotent, pluripotent, multipotent, oligopotent or unipotent stem cell. In another example, the present methods can be used to promote ventricular cardiomyocyte formation from an embryonic stem cell, an induced pluripotent stem cell, a fetal stem cell or an adult stem cell. In still another example, the present methods can be used to promote ventricular cardiomyocyte formation from a mammalian stem cell such as a human stem cell. In yet another example, the present methods can be used to promote ventricular cardiomyocyte formation from a human embryonic stem cell or a human induced pluripotent stem cell.

The stem cell can be induced to differentiate to form mesoderm by any suitable treatment or agent. In one example, the stem cell is induced to differentiate to form mesoderm by contacting an undifferentiated stem cell with basic fibroblast growth factor (bFGF), BMP 4 and/or activin A. In another example, the stem cell is induced to differentiate to form mesoderm by contacting an undifferentiated stem cell with basic fibroblast growth factor (bFGF), BMP 4 and activin A. The stem cell can be treated with bFGF, BMP 4 and activin A in any suitable order. For example, the stem cell can be induced to differentiate to form mesoderm by contacting an undifferentiated stem cell with basic fibroblast growth factor (bFGF) and BMP 4 before the stem cell is contacted with activin A. In another example, the stem cell can be differentiated to form mesoderm by contacting an undifferentiated stem cell with wnt-3a (Tran, T. H. et al. Wnt3a-induced mesoderm formation and cardiomyogenesis in human embryonic stem cells. *Stem Cells* 27, 1869-1878 (2009)), or a small molecule which acts or functions like wnt-3a, such as Bio or CHIR99021.

The present methods can further comprise contacting the stem cell with a BMP antagonist to enhance the cardiac differentiation efficiency. Any suitable BMP antagonist can be used in the present methods. For example, a BMP 4 antagonist can be used. In another example, the BMP antagonist is Noggin. In still another example, the BMP antagonist is Chordin, Tsg, a member of DAN family (Yanagita, M. BMP antagonists: their roles in development and involvement in pathophysiology. *Cytokine Growth Factor Rev* 16, 309-317, (2005)), BMP soluble receptors, such as BMPR1A and BMPR1B, or a small molecule which acts or functions like BMP antagonist, such as Dorsomorphin (Hao, J. et al. Dorsomorphin, a selective small molecule inhibitor of BMP signaling, promotes cardiomyogenesis in embryonic stem cells. *PLoS One* 3, e2904 (2008)).

The retinoic acid signaling pathway in the stem cell can be inhibited by any suitable treatment or agent. In one example, the retinoic acid signaling pathway is inhibited by contacting the stem cell with a retinoic acid antagonist, a retinoic acid receptor antagonist or a retinoic X receptor antagonist. In another example, the retinoic acid signaling pathway is inhibited by contacting the stem cell with a pan-retinoic acid receptor antagonist, e.g., BMS-189453. In still another example, the retinoic acid signaling pathway is inhibited by contacting the stem cell with BMS-453, AGN194310, ANG193109, Ro41-5253, SR11335, 9-cis-retinoic acid, or a small molecule that inhibits retinoic acid synthesis, such as disulfiram and citral. In yet another example, the retinoic acid signaling pathway is inhibited by reducing or depleting vitamin A in the culture medium for the stem cell.

In one specific example, the stem cell is a human embryonic stem cell or a human induced pluripotent stem cell, the BMP antagonist is Noggin and the retinoic acid signaling pathway is inhibited by contacting the stem cell with BMS-189453.

The present methods can further comprise contacting the stem cell with a wnt inhibitor to differentiate the stem cell into a ventricular cardiomyocyte. Any suitable wnt inhibitor can be used. In one example, the wnt inhibitor is dickkopf homolog 1 (DKK1).

In one embodiment, the present disclosure provides a method for generating a ventricular cardiomyocyte from a stem cell, which method comprises: 1) contacting a stem cell with an agent, e.g., bFGF and BMP 4, to initiate stem cell differentiation; 2) contacting the stem cell treated by the agent, e.g., bFGF and BMP 4, with another agent, e.g., activin A, to form mesoderm; 3) contacting the stem cell that has differentiated to form mesoderm with a BMP antagonist such as Noggin, to enhance cardiac differentiation efficiency of the stem cell; 4) inhibiting retinoic acid signaling pathway in the stem cell treated by BMP antagonist, e.g., Noggin, to promote ventricular cardiomyocyte formation; and 5) contacting the stem cell treated by BMP antagonist, e.g., Noggin, with a wnt inhibitor such as DKK1 to differentiate the stem cell into a ventricular cardiomyocyte. Ventricular cardiomyocytes produced by the above method are also provided.

In another embodiment, the present disclosure provides a method for generating a ventricular cardiomyocyte from a stem cell, which method comprises: 1) contacting a stem cell with bFGF and BMP 4; 2) contacting the stem cell treated by bFGF and BMP 4 with activin A; 3) contacting the stem cell that has been treated by activin A with Noggin; 4) inhibiting retinoic acid signaling pathway in the stem cell treated by Noggin; and 5) contacting the stem cell treated by Noggin with DKK1. Ventricular cardiomyocytes produced by the above method are also provided.

A ventricular cardiomyocyte produced by the above methods is also provided. The ventricular cardiomyocyte can have elevated expression level of a ventricular specific gene, e.g., IRX-4 or MLC-2v, embryonic ventricular-like action potentials (AP) and/or $Ca^{2+}$ spark pattern typical of a ventricular cardiomyocyte.

A composition comprising a stem cell that has differentiated to form mesoderm and treated with an exogenous agent that inhibits retinoic acid signaling pathway in the stem cell is further provided. The exogenous agent can be any suitable agent that inhibits retinoic acid signaling pathway in the stem cell. In one example, the exogenous agent that inhibits retinoic acid signaling pathway in the stem cell is a pan-retinoic acid receptor antagonist, e.g., BMS-189453. In another example, the retinoic acid signaling pathway is inhibited by contacting the stem cell with BMS-453, AGN194310, ANG193109, Ro41-5253, SR11335, 9-cis-retinoic acid, or a small molecule that inhibits retinoic acid synthesis, such as disulfiram and citral.

D. Methods and Compositions for Promoting Atrial Cardiomyocyte Formation and Atrial Cardiomyocyte Produced Thereof In still another aspect, the present disclosure provides a method for promoting atrial cardiomyocyte formation from a stem cell, which method comprises stimulating or not inhibiting retinoic acid signaling pathway in a stem cell that has differentiated to form mesoderm.

The present methods can be used to promote atrial cardiomyocyte formation from any suitable stem cell. In one example, the present methods can be used to promote atrial cardiomyocyte formation from a totipotent, pluripotent, multipotent, oligopotent or unipotent stem cell. In another example, the present methods can be used to promote atrial cardiomyocyte formation from an embryonic stem cell, an induced pluripotent stem cell, a fetal stem cell or an adult stem cell. In still another example, the present methods can be used to promote atrial cardiomyocyte formation from a mammalian stem cell such as a human stem cell. In yet another example, the present methods can be used to promote atrial cardiomyocyte formation from a human embryonic stem cell or a human induced pluripotent stem cell.

The stem cell can be induced to differentiate to form mesoderm by any suitable treatment or agent. In one example, the stem cell is induced to differentiate to form mesoderm by contacting an undifferentiated stem cell with basic fibroblast growth factor (bFGF), BMP 4 and/or activin A. In another example, the stem cell is induced to differentiate to form mesoderm by contacting an undifferentiated stem cell with basic fibroblast growth factor (bFGF), BMP 4 and activin A. The stem cell can be treated with bFGF, BMP 4 and activin A in any suitable order. For example, the stem cell is induced to differentiate to form mesoderm by contacting an undifferentiated stem cell with basic fibroblast growth factor (bFGF) and BMP 4 before the stem cell is contacted with activin A. In another example, the stem cell can be differentiated to form mesoderm by contacting an undifferentiated stem cell with wnt-3a (Tran, T. H. et al. Wnt3a-induced mesoderm formation and cardiomyogenesis in human embryonic stem cells. *Stem Cells* 27, 1869-1878 (2009)), or a small molecule which acts or functions like wnt-3a, such as Bio or CHIR99021.

The present methods can further comprise contacting the stem cell with a BMP antagonist to enhance the cardiac differentiation efficiency. Any suitable BMP antagonist can be used in the present methods. For example, a BMP 4 antagonist can be used. In another example, the BMP antagonist is Noggin. In still another example, the BMP antagonist is Chordin, Tsg, a member of DAN family (Yanagita, M. BMP antagonists: their roles in development and involvement in pathophysiology. *Cytokine Growth Factor Rev* 16, 309-317, (2005)), BMP soluble receptors, such as BMPR1A and BMPR1B, or a small molecule which acts or functions like BMP antagonist, such as Dorsomorphin (Hao, J. et al. Dorsomorphin, a selective small molecule inhibitor of BMP signaling, promotes cardiomyogenesis in embryonic stem cells. *PLoS One* 3, e2904 (2008)).

The retinoic acid signaling pathway in the stem cell can be stimulated by any suitable treatment or agent. In one example, the retinoic acid signaling pathway in the stem cell is stimulated by contacting the stem cell with retinoic acid or vitamin A. In another example, the retinoic acid signaling pathway in the stem cell is stimulated by contacting the stem cell with a retinoic acid receptor agonist, such as LG100268 and LGD1069.

In one specific example, the stem cell is a human embryonic stem cell or a human induced pluripotent stem cell, the BMP antagonist is Noggin and the retinoic acid signaling pathway is stimulated by contacting the stem cell with retinoic acid or vitamin A.

The present methods can further comprise contacting the stem cell with a wnt inhibitor to differentiate the stem cell into an atrial cardiomyocyte. Any suitable wnt inhibitor can be used. In one example, the wnt inhibitor is dickkopf homolog 1 (DKK1).

In one embodiment, the present disclosure provides a method for generating an atrial cardiomyocyte from a stem cell, which method comprises: 1) contacting a stem cell with an agent, e.g., bFGF and BMP 4, to initiate stem cell differentiation; 2) contacting the stem cell treated by the agent, e.g., bFGF and BMP 4, with another agent, e.g., activin A, to form mesoderm; 3) contacting the stem cell that has differentiated to form mesoderm with a BMP antagonist such as Noggin, to enhance cardiac differentiation efficiency of the stem cell; 4) stimulating or not inhibiting retinoic acid signaling pathway in the stem cell treated by Noggin to promote atrial cardiomyocyte formation; and 5) contacting the stem cell treated by Noggin with DKK1 to differentiate the stem cell into an atrial cardiomyocyte. Atrial cardiomyocytes produced by the above method are also provided.

In another embodiment, the present disclosure provides a method for generating an atrial cardiomyocyte from a stem cell, which method comprises: 1) contacting a stem cell with bFGF and BMP 4; 2) contacting the stem cell treated by bFGF and BMP 4 with activin A; 3) contacting the stem cell that has been treated by activin A with Noggin; 4) stimulating or not inhibiting retinoic acid signaling pathway in the stem cell treated by Noggin; and 5) contacting the stem cell treated by Noggin with DKK1. Atrial cardiomyocytes produced by the above method are also provided.

An atrial cardiomyocyte produced by the above methods is also provided. In one example, an atrial cardiomyocyte can have embryonic atrial-like action potentials (AP) and/or $Ca^{2+}$ spark pattern typical of an atrial cardiomyocyte.

A composition comprising a stem cell that has differentiated to form mesoderm and treated with an exogenous agent that stimulates retinoic acid signaling pathway in the stem cell is further provided. Any suitable exogenous agent can be used to stimulate retinoic acid signaling pathway in the stem cell. In one example, the exogenous agent that stimulates retinoic acid signaling pathway in the stem cell is retinoic acid or vitamin A.

E. Pharmaceutical Compositions and Uses of the Cardiomyocytes

The cardiomyocytes can be used for any suitable purposes. In one aspect, the present disclosure provides a pharmaceutical composition for treating a cardiac injury or disorder, which pharmaceutical composition comprises an effective amount of the cardiomyocytes produced by the above methods, and optionally a pharmaceutically acceptable carrier or expicient. In one embodiment, the pharmaceutical composition comprises a mixture of atrial and ventricular cardiomyocytes. In another embodiment, the pharmaceutical composition comprises at least about 50%, preferably, at least about 60%, 70%, 80%, 90%, 95%, 99%, or 100% atrial cardiomyocytes. In still another embodiment, the pharmaceutical composition comprises at least about 50%, preferably, at least about 60%, 70%, 80%, 90%, 95%, 99%, or 100% ventricular cardiomyocytes.

In another aspect, the present disclosure provides a method for treating a cardiac injury or disorder in a subject, e.g., a human, which method comprises administering, to a subject to which such treatment is needed or desirable, an effective amount of the above pharmaceutical composition.

The formulation, dosage and route of administration of the cardiomyocytes, whether predominantly atrial cardiomyocytes, predominantly ventricular cardiomyocytes or a mixture of atrial and ventricular cardiomyocytes, preferably in the form of pharmaceutical compositions, can be determined according to the methods known in the art (see e.g., *Remington: The Science and Practice of Pharmacy*, Alfonso R. Gennaro (Editor) Mack Publishing Company, April 1997; *Therapeutic Peptides and Proteins: Formulation, Processing, and Delivery Systems*, Banga, 1999; and *Pharmaceutical Formulation Development of Peptides and Proteins*, Hovgaard and Frkjr (Ed.), Taylor & Francis, Inc., 2000; *Medical Applications of Liposomes*, Lasic and Papahadjopoulos (Ed.), Elsevier Science, 1998; *Textbook of Gene Therapy*, Jain, Hogrefe & Huber Publishers, 1998; *Adenoviruses: Basic Biology to Gene Therapy*, Vol. 15, Seth, Landes Bioscience, 1999; *Biopharmaceutical Drug Design and Development*, Wu-Pong and Rojanasakul (Ed.), Humana Press, 1999; *Therapeutic Angiogenesis: From Basic Science to the Clinic*, Vol. 28, Dole et al. (Ed.), Springer-Verlag New York, 1999). In specific embodiments, the cardiomyocytes can be combined or formulated with endothelial cells, smooth muscle cells and/or fibroblast cells, and implanted into a heart. The cell or tissue patch can be transplanted by direct injection to the infarct area, injection with a catheter or implanted as a cardio-patch by a surgery. Preferably, the cardiomyocytes are formed from stem cells of the subject that is to be treated. Also preferably, the endothelial cells, smooth muscle cells and/or fibroblast cells are also obtained or derived from the subject that is to be treated, e.g., formed from stem cells of the subject that is to be treated.

The cardiomyocytes can be formulated for any suitable route of administration. In one example, the cardiomyocytes are administered by surgery or cell transplantation. The most suitable route in any given case will depend on the nature and severity of the condition being treated and on the nature of the particular cardiomyocytes which are being used.

The cardiomyocytes can be administered alone. Alternatively and preferably, the cardiomyocytes are co-administered with a pharmaceutically acceptable carrier or excipient. Any suitable pharmaceutically acceptable carrier or excipient can be used in the present method (See e.g., *Remington: The Science and Practice of Pharmacy*, Alfonso R. Gennaro (Editor) Mack Publishing Company, April 1997).

The present method can be used alone. Alternatively, the present method can be used in combination with other agent suitable for preventing, treating or delaying a cardiac injury, disease or disorder. Such other agent can be used before, with or after the administration of the cardiomyocytes. For example, the cardiomyocytes can be co-administered with such other agent.

According to the present invention, the cardiomyocytes, alone or in combination with other agents, carriers or excipients, may be formulated for any suitable administration route, such as surgery or cell transplantation. The method may employ formulations for administration in unit dosage form, in ampoules or in multidose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, sterile pyrogen-free water or other solvents, before use.

Pharmaceutically acceptable compositions and methods for their administration that may be employed for use in this invention include, but are not limited to those described in U.S. Pat. Nos. 5,736,154; 6,197,801 B1; 5,741,511; 5,886,039; 5,941,868; 6,258,374 B1; and 5,686,102.

The magnitude of a therapeutic dose in the treatment or prevention will vary with the severity of the condition to be treated and the route of administration. The dose, and perhaps dose frequency, will also vary according to age, body weight, condition and response of the individual patient.

It should be noted that the attending physician would know how to and when to terminate, interrupt or adjust therapy to lower dosage due to toxicity, or adverse effects. Conversely, the physician would also know how to and when to adjust treatment to higher levels if the clinical response is not adequate (precluding toxic side effects).

Any suitable route of administration may be used. Dosage forms include tablets, troches, cachet, dispersions, suspensions, solutions, capsules, patches, and the like. See, Remington's Pharmaceutical Sciences.

In practical use, the cardiomyocytes, alone or in combination with other agents, may be combined as the active in intimate admixture with a pharmaceutical carrier or excipient, such as beta-cyclodextrin and 2-hydroxy-propyl-beta-cyclodextrin, according to conventional pharmaceutical compounding techniques. The carrier may take a wide form of preparation desired for suitable administration. In preparing compositions for parenteral dosage form, such as intravenous injection or infusion, similar pharmaceutical media may be employed, water, glycols, oils, buffers, sugar, preservatives, liposomes, and the like known to those of skill in the art. Examples of such parenteral compositions include, but are not limited to dextrose 5% w/v, normal saline or other solutions. The total dose of the cardiomyocytes, alone or in combination with other agents to be administered may be administered in a vial of fluid, ranging from about $1\times10^3$ to $1\times10^{10}$ cells, e.g., $1\times10^3$, $1\times10^4$, $1\times10^5$, $1\times10^6$, $1\times10^7$, $1\times10^8$, $1\times10^9$, or $1\times10^{10}$ cells, or any subrange within the range of $1\times10^3$ to $1\times10^{10}$ cells.

The invention also provides for kits for carrying out the therapeutic regimens of the invention. Such kits comprise in one or more containers therapeutically effective amounts of the cardiomyocytes, alone or in combination with other agents, in pharmaceutically acceptable form. Preferred pharmaceutical forms would be in combination with sterile saline, dextrose solution, or buffered solution, or other pharmaceutically acceptable sterile fluid. Alternatively, the composition may be lyophilized or dessicated; in this instance, the kit optionally further comprises in a container a pharmaceutically acceptable solution, preferably sterile, to reconstitute the complex to form a solution for injection purposes. Exemplary pharmaceutically acceptable solutions are saline and dextrose solution.

In another embodiment, a kit of the invention further comprises a needle or syringe, preferably packaged in sterile form, for injecting the composition, and/or a packaged alcohol pad. Instructions are optionally included for administration of composition by a physician or by the patient.

F. Other Uses of the Cardiomyocytes

The cardiomyocytes can be used for any suitable purposes. In one embodiment, the present disclosure provides a method for identifying a modulator of a cardiomyocyte, which method comprises: 1) contacting a cardiomyocyte produced by the above methods with a test substance and measuring the effect of the test substance on a property of the cardiomyocyte; 2) measuring the property of the cardiomyocyte not contacted with the test substance; whereby the property of the cardiomyocyte contacted with the test substance is different from that of the cardiomyocyte not contacted with the test substance identifies the test substance as a modulator, e.g., a stimulator or inhibitor, of the property of the cardiomyocyte. In one example, an increase of the property of the cardiomyocyte contacted with the test substance relative to that of the cardiomyocyte not contacted with the test substance identifies the test substance as a stimulator of the property of the cardiomyocyte. In another example, a decrease of the property of the cardiomyocyte contacted with the test substance relative to that of the cardiomyocyte not contacted with the test substance identifies the test substance as an inhibitor of the property of the cardiomyocyte.

The method can be conducted in any suitable format. Preferably, the method is conducted in a high-throughput screening (HTS) format.

G. Examples

Abstract

Although cell transplantation studies have suggested promising therapeutic potentials for myocardial infarction, the incapability to obtain relatively homogeneous ventricular myocytes for transplantation is one major obstacle to the development of clinical therapies for myocardial repair[1]. Human embryonic stem cell (hESC) is a promising source of cardiomyocytes. Here we report that retinoid signaling regulates the fate specification of atrial versus ventricular myocytes during cardiac differentiation of hESCs. We found that both Noggin and pan-retinoic acid receptor antagonist BMS-189453 (RAi) significantly increase the cardiac differentiation efficiency of hESCs[2]. Investigating retinoid function by comparing Noggin+RAi-treated cultures with Noggin+RA-treated cultures, our results show that the expression level of the ventricular-specific gene IRX-4 was radically elevated in Noggin+RAi-treated cultures[3], and MLC-2v, another ventricular-specific marker[4,5], was expressed in the majority of the cardiomyocytes in Noggin+RAi-treated cultures, but not in those of Noggin+RA-treated cultures. Flow cytometry analysis and electrophysiological studies indicated that with 64±0.88% (mean±s.e.m) cardiac differentiation efficiency, 83% of the cardiomyocytes in Noggin+RAi-treated cultures had embryonic ventricular-like action potentials (AP); while, with 50±1.76% cardiac differentiation efficiency, 94% of those in Noggin+RA-treated cultures had embryonic atrial-like APs. These results were further confirmed by imaging studies on the patterns and properties of the $Ca^{2+}$ sparks of the cardiomyocytes in those two differently treated cultures. These findings demonstrating that retinoid signaling specifies atrial versus ventricular differentiation of hESCs, and relatively homogeneous embryonic atrial and ventricular like myocyte populations can be efficiently derived from hESCs by specifically regulating Noggin and retinoid signals.

Summary

Although cell transplantation studies have suggested promising therapeutic potentials for myocardial infarction, the incapability to obtain relatively homogeneous ventricular myocytes for transplantation is one major obstacle to the development of clinical therapies for myocardial repair[1]. Human embryonic stem cell (hESC) is a promising source of cardiomyocytes. Here we report that retinoid signaling regulates the fate specification of atrial versus ventricular myocytes during cardiac differentiation of hESCs. We found that both Noggin and pan-retinoic acid receptor antagonist BMS-189453 (RAi) significantly increase the cardiac differentiation efficiency of hESCs[2]. Investigating retinoid function by comparing Noggin+RAi-treated cultures with Noggin+RA-treated cultures, our results show that the expression level of the ventricular-specific gene IRX-4 was radically elevated in Noggin+RAi-treated cultures[3], and MLC-2v, another ventricular-specific marker[4,5], was expressed in the majority of the cardiomyocytes in Noggin+RAi-treated cultures, but not in those of Noggin+RA-treated cultures. Flow cytometry analysis and electrophysiological studies indicated that with 64±0.88% (mean±s.e.m) cardiac differentiation efficiency, 83% of the cardiomyocytes in Noggin+RAi-treated cultures had embryonic ventricular-like action potentials (AP); while, with 50±1.76% cardiac differentiation efficiency, 94% of those in Noggin+RA-treated cultures had embryonic atrial-like APs. These results were further confirmed by imaging studies on the patterns and properties of the $Ca^{2+}$ sparks of the cardiomyocytes in those two differently treated cultures. These findings demonstrating that retinoid signaling specifies atrial versus ventricular differentiation of hESCs, and relatively homogeneous embryonic atrial and ventricular like myocyte populations can be efficiently derived from hESCs by specifically influencing BMP and retinoid signaling cascades.

Material and Methods

Maintenance and Differentiation of hESCs.

Undifferentiated hESC line H7 from the WiCell Research Institute was maintained on matrigel-coated plates, as previously described[37]. In the basic cardiac induction protocol (BP), undifferentiated hESCs were seeded on gelatin-coated plates at a density of $1-5\times10^5$ cells/cm$^2$ and cultured with mouse embryonic fibroblast conditioned medium for 3 days until fully confluent. To initiate cell differentiation, the medium was changed to RPMI1640, supplemented with B27 (Invitrogen). Cells were treated with 25 ng/ml BMP4 and 6 ng/ml bFGF at day 1, 100 ng/ml activin A at day 2, and 200 ng/ml DKK1 (R&D Systems) from day 6 to day 11. The medium was changed every 3 days after day 11 (FIG. 1). 250 ng/ml Noggin, 1 μM RA (Sigma) or 1 μM RAi were added to the cell culture at the times specified in FIGS. 1A-C. Spontaneous beating clusters were typically observed at days 10 to 11. Cardiac differentiation efficiency was analyzed on day 14 with CTNT antibody staining and flow cytometry.

Single Cell Preparation of hES-Derived Cardiomyocytes.

Six (60) to 90 day-old differentiated cultures were washed in a low $Ca^{2+}$ solution, and then incubated in an enzyme solution for 20 min at 37° C. The dissociation was completed in KB solution by gently shaking for 40 min at room temperature. The isolated cells were resuspended in DMEM plus 10% FBS, and transferred on 0.1% gelatin-coated glass coverslips, and then kept in an incubator at 37° C., 5% $CO_2$. The composition of the low $Ca^{2+}$ solution was (in mM):120 NaCl, 5.4 KCl, 5 MgSO$_4$, 5 Na pyruvate, 20 glucose, 20 taurine, 10 HEPES. The pH was adjusted to 7.3 with NaOH. KB solution contained (in mM): 85 KCl, 30 K$_2$HPO$_4$, 5 MgSO$_4$, 1 EGTA, 2 Na$_2$ATP, 5 Na pyruvate, 20 glucose, 20 taurine, 5 creatine, adjusted to pH 7.3 with KOH.

Electrophysiological Measurements and Confocal $Ca^{2+}$ Imaging.

Action potentials of cardiomyocytes were recorded in a whole-cell patch clamp configuration, using an Axon 200B amplifier (Axon Instruments) at room temperature. Data were digitized at 20 kHz and filtered at 2 kHz, and were analyzed by PClamp 9.0. Patch pipettes (2-4MΩ resistance) were filled with an intracellular solution containing (in mM) 50 KCl, 60 K-Aspartate, 1 $MgCl_2$, 3 $Na_2ATP$, 10 EGTA, 10 mM HEPES, adjusted to pH 7.3 with KOH. Normal Tyrode's solution was used as an extracellular solution and contained (in mM) 140 NaCl, 5 KCl, 1 $CaCl_2$, 1 MgCl2, 10 glucose, 10 HEPES, adjusted to pH 7.4 with NaOH.

For $Ca^{2+}$ confocal imaging, myocytes were incubated with Fluo-4AM (10 μM/L; Molecular Probes) for 10 min at room temperature and then perfused with extracellular buffer for about 30 min. $Ca^{2+}$ imaging studies were performed on a Leica SP5 confocal microscope equipped with an argon laser (488 nm) at a magnification of 40× using a 1.25NA oil immersion objective. Spontaneous $Ca^{2+}$ sparks and $Ca^{2+}$ transients were recorded using linescans, obtained at 0.5 ms per line. Images were processed and analyzed using both MATLAB 7.1 software (MathWorks) and ImageJ (Scioncorp). Detection criteria of 3.8×SD for $Ca^{2+}$ sparks were set, and automated counting of $Ca^{2+}$ sparks was performed using the Sparkmaster plug-in for ImageJ[38].

Flow Cytometry.

Differentiated cell clusters were dissociated into single cells with 0.25% trypsin-EDTA, which were then fixed and stained with anti-human CTNT antibody (R&D Systems) and goat anti-mouse FITC-conjugated secondary antibody (Santa Cruz) in PBS plus 0.5% BSA and 0.1% saponin (Sigma) at 4° C. Stained cells were kept in 4% paraformaldehyde for subsequent quantitative analysis. Data were collected using FACScalibur (Becton Dickinson) and analyzed with FlowJo software (Treestar).

Real-Time RT-PCR.

Total RNA was isolated using Qiagen's RNeasy Plus Mini kit from a single well of a 24-well plate of differentiated hES cells. Then 1 μg of total RNA was reverse transcribed with SuperScript III First-Strand Synthesis System (Invitrogen). RT-PCR was carried out using rTaq DNA Polymerase (Takara). Real-time PCR was performed in triplicate using 2× QuantiFast SYBR Green I PCR Master Mix (Qiagen) on a Rotor Gene 6200 Real-Time PCR Machine (Corbett), with an annealing temperature of 60° C. The expression of each gene was normalized to GAPDH gene expression. Primer sequences are listed in Table 2.

Immunofluorescence.

Sixty (60) day-old differentiated cultures were digested with 0.25% trypsin-EDTA, and the cells were plated on gelatin-coated coverslips for 5 days, allowing full attachment to occur. Cells were then fixed in 4% paraformaldehyde, and incubated with primary antibodies of mouse anti-human CTNT (R&D systems), mouse anti-human α-Actinin (Sigma), mouse anti-human β-MHC (ATCC), mouse anti-human MLC-2a (Synaptic Systems), or rabbit anti-human MLC-2v (ProteinTech Group). Goat anti-mouse secondary antibody conjugated with DyLight 488 (Santa Cruz Biotechnology) and goat anti-rabbit secondary antibody conjugated with Tritc (Santa Cruz Biotechnology) were used as needed. After the nuclei were counterstained with 4',6-diamidino-2-phenylindole (DAPI, Sigma), immunofluorescence images were visualized and recorded using an Olympus microscope system X51 or Olympus LSCM FV1000.

Western Blotting.

One well of a 24-well plate of 60 day-old differentiated cells was lysed with RIPA lysis buffer (Biomiga) for Western blotting. Blots were incubated with mouse anti-human CTNT, mouse anti-human β-MHC, rabbit anti-human MLC-2v, goat anti-ANF, mouse anti-human MLC-2a, mouse anti-human β-actin, rabbit anti-phospho smad1/5/8 and rabbit anti-smad1/5/8 separately, and then with HRP-conjugated goat anti-mouse or anti-rabbit antibody.

TABLE 1

| AP parameters recorded from hESC derived cardiomyoctes. | | | | | |
|---|---|---|---|---|---|
| | n (cell) | Vmax (V/s) | APA (mV) | APD90 (ms) | MDP (mV) |
| Nodal-like | 6 | 7.3 ± 4.2 | 74.5 ± 8.9# | 147.6 ± 26.8$ | −51.3 ± 8.2† |
| Atrial-like | 36 | 12.8 ± 3.1* | 81.6 ± 11.5# | 168.8 ± 26.8$ | −55.5 ± 6.5† |
| Ventricular-like | 42 | 11.4 ± 2.8* | 86.8 ± 12.4# | 285.8 ± 52.6$ | −62.3 ± 8.6† |

Table 1 AP parameters recorded from hESC-derived cardiomyoctes. Data are means±se. n indicates the number of cells tested. Vmax, maximum rate of AP increase; APA. AP amplitude; APD90, AP duration measured at 90% repolarization; MDP, maximum diastolic potential. *P<0.05 compared with nodal-like; # P<0.05 compared with each other; $P<0.01 compared with each other; and †P<0.05 compared with each other.

TABLE 2

| Primer sequences used for qPCR. | | | |
|---|---|---|---|
| Gene | Forward Primer | Reverse Primer | Tm |
| NXK2.5 | acctcaacagctccctgactct (SEQ ID NO: 1) | ataatcgccgccacaaactctcc (SEQ ID NO: 2) | 60° C. |
| CTNT | ttcaccaaagatctgctcctcgct (SEQ ID NO: 3) | ttattactggtgtggagtgggtgtgg (SEQ ID NO: 4) | 60° C. |
| IRX4 | ttccgttctgaagcgtggtc (SEQ ID NO: 5) | tgaagcaggcaattattggtgt (SEQ ID NO: 6) | 60° C. |
| GAPDH | gaaatcccatcaccatcttccagg (SEQ ID NO: 7) | gagcccagccttctccatg (SEQ ID NO: 8) | 60° C. |

Results

Based on the previous studies, we hypothesized that inhibition of BMP pathway after initiation of hESC differentiation and blocking retinoic acid signaling promotes cardiogenesis; Retinoid signaling also regulates atrial versus ventricular differentiation of hESCs. To test these hypotheses, we admitted Noggin, RA and its inhibitor RAi to the cardiac differentiation cultures at different time intervals, and investigated their effects on cardiogenesis and cardiac subtype specification of hESC derivatives. Our results show that inhibition both BMP and RA signals with Noggin and RAi significantly promote cardiogenesis, and retinoid signaling controls the atrial versus ventricular specification of differentiated hESCs. In addition to providing important insights into the mechanisms that specify cardiac subtypes, our findings also demonstrated the direct differentiation of relatively homogeneous embryonic atrial and ventricular-like myocytes from hESCs.

Noggin and RA Antagonist BMS189453 Promote Cardiogenesis of Differentiated hESCs.

In order to investigate its functions in cardiac differentiation, Noggin was systematically added to cardiomyocyte-differentiating hESC cultures generated by a protocol developed in our laboratory (see Methods for detailed description) for different time intervals from days 2 to 5. Results show that cardiac differentiation was slightly repressed when Noggin was present between days 2 and 3, but significantly promoted between days 2.5 and 4.5. Highest cardiac differentiation efficiencies were achieved between days 4 and 5 (FIG. 1B). Western blot for phosphorylated Smad1,5,8 indicated that Noggin reduced the activities of BMP signaling (data not shown). Therefore, inhibition of BMP signaling promotes cardiogenesis in hESCs after the initiation of differentiation.

Previous findings that RA signal restricts embryonic cardiac progenitor raise the possibility that inhibition of RA signaling during cardiac differentiation of hESCs could promote cardiogenesis. Vitamin A, the substrate for RA synthesis, and RALDH2, the enzyme responsible for RA synthesis[24], were both present in our cultures (data not shown), suggesting the potential of RA signaling activation. We therefore tested the effects of RA inhibition on promoting hESC cardiac differentiation by adding RAi to our cardiomyocyte-differentiating cultures between days 4 and 9 at the time points indicated in FIG. 1C. Flow cytometry showed that cardiac differentiation was markedly increased when RAi was added between days 6 to 9 (FIG. 1C), demonstrating that inhibition of RA signaling promotes cardiac differentiation of hESCs.

Next we combined Noggin-treatment on days 4 and 5, and RAi-treatment from days 6 to 8. Flow cytometry of CTNT+ cells from day 14 cultures showed that, with Noggin alone, the differentiation efficiency was 50%±3.06% (mean±s.e.m), and that this efficiency increased to 73%±2.08% when cells were treated with both RAi and Noggin (FIG. 1D). This was confirmed by results from quantitative RT-PCR analysis of day 14 cultures. The expression levels of both CTNT and NKX2.5 were significantly higher in Noggin+RAi-treated cultures than in cultures treated with Noggin alone (FIG. 1E). Immunostaining indicated the expression of typical cardiac markers including CTNT, α-Actinin, MLC-2a, MLC-2v, and β-MHC (FIG. 1F) in cultured cells.

Alternative Retinoid Signals Direct the Differentiation hESCs into Two Distinct Subtype of Cardiomyocytes.

Because the studies of chicken and mouse embryos indicated that retinoid signaling regulates the fate specification of in-flow and out-flow track tissues[5,20-24], we proposed that the activation or inactivation of retinoid signaling directs atrial vs. ventricular fate specification of differentiated hESC cardiac progenitors, and that such a mechanism could be used to efficiently generate either hESC-derived atrial- or ventricular-like myocytes.

To test this hypothesis, either RA or its antagonist, RAi, was added to the Noggin-treated cultures between days 6 to 8 in parallel experiments (FIG. 1A). After 14 days' differentiation, the percentages of CTNT+ cells in Noggin+RA and Noggin+RAi-treated cultures was 50.7%±1.76% and 64.7%±0.88% respectively (FIG. 2A). Despite there is only about 14% difference in the differentiation efficiencies, the size of beating cardiomyocytes in the Noggin+RA-treated cultures was smaller than that of those in the Noggin+RAi-treated cultures (FIG. 2B, D). The beating rate of cardiomyocytes in the Noggin+RA-treated cultures was also faster than that of those in the Noggin+RAi-treated cultures (FIG. 2C and Table 1), suggesting that there were two different subtypes of cardiomyocytes present in these two different cultures. Next, we examined the expression of ventricular-specific genes, IRX4 and MLC-2v, in the two cultures. Quantitative RT-PCR showed that in Noggin+RAi-treated cultures, IRX4 expression started to climb on day 8, and by day 14 it was 10 fold higher than that in the Noggin+RA-treated cultures (FIG. 3A). Immunostaining of 60-day-old cultures showed that MLC-2v was expressed in the majority of CTNT+ cells in Noggin+RAi-treated, but not in Noggin+RA-treated cultures (FIG. 3B), consistent with results from Western blotting indicating that although CTNT was expressed at similar levels in these two cultures, MLC-2v was strongly and only expressed in Noggin+RAi-treated cultures (FIG. 3C). We also compared the expression of cTNT and MLC-2v in Noggin+RAi-treated, Noggin-treated and Noggin+RA-treated cultures with immunostaining and western blots. The results show that Noggin alone treated cultures only about 35% cTNT positive cells are also MLC-2v positive, and with weak MLC-2v expression detected by western blots (FIG. 5). These results indicate that the majority of the cardiomyocytes in Noggin+RAi-treated cultures are embryonic ventricular-like myocytes, whereas the cardiomyocytes differentiated in Noggin+RA-treated cultures are either embryonic nodal- or atrial-like myocytes which do not express MLC-2v. We also examined the expressions of β-MHC, MLC-2a, and Atrial Nutriation Factor (ANF) in RA and RAi treated cultures with western blots, and results showed that β-MHC is evenly expressed in the two cultures, but MLC-2a and ANF are expressed with higher level in RA treated cultures than those in RAi treated cultures (FIG. 6).

Electrophysiolgical Characterization Identifies Embryonic Atrial- and Ventricular-Like Cardiomyocyte Populations Induced by Alternative Retinoid Signals.

Due to a lack of endogenous early atrium-specific genetic markers in mammalian systems[5], we chose to use electrophysiological characters to rigorously identify these two cardiac sub-populations. Based on the morphology and classification of AP properties (Table 1)[6,26], three major types of AP (nodal-like, atrial-like, and ventricular-like) were observed in our study (FIG. 4A). However, the ratios of the three major types of APs were different between Noggin+RA- and Noggin+RAi-treated cultures; 83% of myocytes (n=23) from the cultures treated with Noggin+RAi possessed ventricular-like APs (FIG. 4A, C), in which the duration of APs could be shortened by application of nifedipine, a calcium channel blocker (FIG. 4B, left), while 94% of myocytes (n=19) from Noggin+RA-treated cultures exhibited an atrial-like AP, and the duration of the AP could not be shortened by nifedipine (FIGS. 4A, B right and C). These results demonstrate that the majority of the cardiomyocytes in Noggin+RA-treated culture were embryonic atrial-like myocytes and the majority of those in Noggin+RAi-treated cultures were embryonic ventricular-like myocytes. Interestingly, in both the Noggin+RA and Noggin+RAi-treated cultures, we did not observe the high percentages of cardiomyocytes bearing nodal-like APs reported in previous studies[6,9].

There are important kinetic differences in $Ca^{2+}$ sparks, the elementary unit of cardiomyocyte $Ca^{2+}$ signaling, in atrial versus ventricular myocytes[27,28]. $Ca^{2+}$ sparks are significantly larger and longer lasting in atrial myocytes than those in ventricular myocytes[28,29]. Results of imaging studies indicated that in Noggin+RAi-treated culture 87.5% (14/16) of cells tested displayed $Ca^{2+}$ sparks with relatively low amplitude, fast rise time, short half time decay and small size, typical $Ca^{2+}$ spark properties of ventricular-like myocytes (FIG. 4D, E). On the other hand, in Noggin+RA-treated cultures, 81.8% (18/22) of cells tested displayed $Ca^{2+}$ sparks with higher amplitude, slower rise time, longer half time decay and larger size (FIG. 4D, E), suggesting that the myocytes from Noggin+RA-treated cultures were atrial-like myocytes. The kinetic study of $Ca^{2+}$ release and the ratios of cardiomyocytes bearing those two patterns in the two differently-treated cultures are consistent with, and support, previous AP phenotyping-based cardiac subtype categorization.

Discussion

Our results show that inhibition of BMP signaling after the initiation of cardiac differentiation promotes cardiogenesis of hESCs. This is partially consistent with the studies on mouse embryonic stem cells showing that administrating Noggin before initiation of differentiation promotes cardiogenesis[13]. Further comparing Noggin treated cells with non-treated cells revealed that granulocyte colony-stimulating factor (G-CSF) promotes the proliferation of developing cardiomycotes derived from mouse embryonic stem cells[30]. Noggin sustains undifferentiated proliferation of hESCs[31], and BMP4 is required for mouse embryonic stem cell self-renew[32]. These different self-renewal machineries could be the cause of the differences observed in the cardiac differentiation studies of human and mouse embryonic stem cells.

Even though western blots revealed the differential expressions of ANF and MLC-2a, both genes are expressed in 60 day old Noggin+RA- and Noggin+RAi-treated cultures (FIG. 6). This is consistent with Dr. Rosenthal's statement, which indicated that there is no early atrial specific marker in mouse system. Instead, they used a proximal 840 bp quail SMyHC3 promoter to label the sino-atrial tissue from the earliest stage of heart developing[5].

Previous studies of chicken and mouse embryos have proposed that RA signaling determines sinoatrial cell fate, whereas ventricular fate is specified in the absence of RA[20]. Our study shows that blocking RA signaling induces the expression of the ventricle-specific marker MLC-2v in major hESC-derived cardiomyocytes, and that these cells possess APs and $Ca^{2+}$ sparks typical of ventricular myocytes. Exogenous RA treatment directs the differentiation of hESCs into myocytes which retain characteristic atrial-like APs and large $Ca^{2+}$ sparks or $Ca^{2+}$ transients. Our results demonstrate that the activation or inhibition of retinoid signals instructs atrial versus ventricular specification of differentiating hESCs. Different from our results, previous study shows that RA enhances development of ventricular cardiomyocytes derived from mouse embryonic stem cells[33]. This could represent the differences on the differentiation culture systems used in the two studies, embryoid body procedure versus flat culture system, and the timing when RA is admitted.

Potential risk of ventricular arrhythmias caused by the heterogeneity of hESC-derived cardiomyocytes is one of the major hurdles for application of hESCs to cardiac repair[1,6,10]. Application of relatively homogeneous ventricular myocytes derived from hESCs in myocardial repair has great potential to reduce this risk, removing one of the major barriers for developing hESC based myocardial repair strategy. Recent advance in tissue engineering, which shows that mouse ventricular progenitor cells can be isolated from mouse embryonic stem cell derivatives using a genetic labeling approach, and are used to generate functional ventricular muscles[34], suggests that human functional ventricular heart muscles can be generated with embryonic ventricular-like mycoytes directly differentiated from hESCs. With a chemical defined culture system and no genetic manipulation, the direct differentiation procedures we developed would be easy to employed in clinical studies of myocardial repair. Another challenge for developing hESC based myocardial repair is to develop the biotechnology for rapidly generating the large amounts of ventricular myocytes needed for transplantation. Our study demonstrated the efficient differentiation of embryonic atrial- and ventricular-like myocytes from hESCs by eliminating embryoid body procedure, a time consuming step which is commonly used in cardiac differentiation of embryonic stem cells. If combined together with induced pluripotent stem (iPS) cell technology[35,36], programmed differentiation of atrial- and ventricular-like myocytes could be used to develop not only safe cell sources for personalized cardiac repair, but could also provide cellular models for the study of genetic atrial or ventricular diseases.

REFERENCES

1 Chen, H. S., Kim, C. & Mercola, M. Electrophysiological challenges of cell-based myocardial repair. *Circulation* 120, 2496-2508 (2009).
2 Schulze, G. E. et al. BMS-189453, a novel retinoid receptor antagonist, is a potent testicular toxin. *Toxicol Sci* 59, 297-308 (2001).
3 Bao, Z. Z., Bruneau, B. G., Seidman, J. G., Seidman, C. E. & Cepko, C. L. Regulation of chamber-specific gene expression in the developing heart by Irx4. *Science* 283, 1161-1164 (1999).
4 Fu, J. D. et al. Na+/Ca2+ exchanger is a determinant of excitation-contraction coupling in human embryonic stem cell-derived ventricular cardiomyocytes. *Stem Cells Dev* (2009).
5 Xavier-Neto, J. et al. A retinoic acid-inducible transgenic marker of sino-atrial development in the mouse heart. *Development* 126, 2677-2687 (1999).
6 He, J. Q., Ma, Y., Lee, Y., Thomson, J. A. & Kamp, T. J. Human embryonic stem cells develop into multiple types of cardiac myocytes: action potential characterization. *Circ Res* 93, 32-39 (2003).
7 Laflamme, M. A. et al. Cardiomyocytes derived from human embryonic stem cells in pro-survival factors enhance function of infarcted rat hearts. *Nat Biotechnol* 25, 1015-1024 (2007).
8 Yang, L. et al. Human cardiovascular progenitor cells develop from a KDR+ embryonic-stem-cell-derived population. *Nature* 453, 524-528 (2008).

9 Zhu, W. Z. et al. Neuregulin/ErbB Signaling Regulates Cardiac Subtype Specification in Differentiating Human Embryonic Stem Cells. *Circ Res* (2010).
10 Kehat, I. et al. Electromechanical integration of cardiomyocytes derived from human embryonic stem cells. *Nat Biotechnol* 22, 1282-1289 (2004).
11 Tran, T. H. et al. Wnt3a-induced mesoderm formation and cardiomyogenesis in human embryonic stem cells. *Stem Cells* 27, 1869-1878 (2009).
12 Reppel, M. et al. Effect of cardioactive drugs on action potential generation and propagation in embryonic stem cell-derived cardiomyocytes. *Cell Physiol Biochem* 19, 213-224 (2007).
13 Yuasa, S. et al. Transient inhibition of BMP signaling by Noggin induces cardiomyocyte differentiation of mouse embryonic stem cells. *Nat Biotechnol* 23, 607-611 (2005).
14 Marvin, M. J., Di Rocco, G., Gardiner, A., Bush, S. M. & Lassar, A. B. Inhibition of Wnt activity induces heart formation from posterior mesoderm. *Genes Dev* 15, 316-327 (2001).
15 Schneider, V. A. & Mercola, M. Wnt antagonism initiates cardiogenesis in *Xenopus laevis*. *Genes Dev* 15, 304-315 (2001).
16 Korol, O., Gupta, R. W. & Mercola, M. A novel activity of the Dickkopf-1 amino terminal domain promotes axial and heart development independently of canonical Wnt inhibition. *Dev Biol* 324, 131-138 (2008).
17 Xu, R. H. et al. BMP4 initiates human embryonic stem cell differentiation to trophoblast. *Nat Biotechnol* 20, 1261-1264 (2002).
18 Zhang, P. et al. Short-term BMP-4 treatment initiates mesoderm induction in human embryonic stem cells. *Blood* 111, 1933-1941 (2008).
19 Keegan, B. R., Feldman, J. L., Begemann, G., Ingham, P. W. & Yelon, D. Retinoic acid signaling restricts the cardiac progenitor pool. *Science* 307, 247-249 (2005).
20 Xavier-Neto, J. et al. Retinoid signaling and cardiac anteroposterior segmentation. *Genesis* 31, 97-104 (2001).
21 Patwardhan, V., Fernandez, S., Montgomery, M. & Litvin, J. The rostro-caudal position of cardiac myocytes affect their fate. *Dev Dyn* 218, 123-135 (2000).
22 Orts-Llorca F, J. C. J. Determination of heart polarity (arterio venous axis) in the chicken embryo. *Roux Arch Entwick-lungsmechanik* 113, 17 (1967).
23 Yutzey, K., Gannon, M. & Bader, D. Diversification of cardiomyogenic cell lineages in vitro. *Dev Biol* 170, 531-541 (1995).
24 Hochgreb, T. et al. A caudorostral wave of RALDH2 conveys anteroposterior information to the cardiac field. *Development* 130, 5363-5374, (2003).
25 Gassanov, N. et al. Retinoid acid-induced effects on atrial and pacemaker cell differentiation and expression of cardiac ion channels. *Differentiation* 76, 971-980 (2008).
26 Maltsev, V. A., Rohwedel, J., Hescheler, J. & Wobus, A. M. Embryonic stem cells differentiate in vitro into cardiomyocytes representing sinusnodal, atrial and ventricular cell types. *Mech Dev* 44, 41-50 (1993).
27 Cheng, H. & Lederer, W. J. Calcium sparks. *Physiol Rev* 88, 1491-1545 (2008).
28 Woo, S. H., Cleemann, L. & Morad, M. Spatiotemporal characteristics of junctional and nonjunctional focal Ca2+ release in rat atrial myocytes. *Circ Res* 92, e1-11 (2003).
29 Cleemann, L., Wang, W. & Morad, M. Two-dimensional confocal images of organization, density, and gating of focal Ca2+ release sites in rat cardiac myocytes. *Proc Natl Acad Sci USA* 95, 10984-10989 (1998).
30 Shimoji, K. et al. G-CSF promotes the proliferation of developing cardiomyocytes in vivo and in derivation from ESCs and iPSCs. *Cell Stem Cell* 6, 227-237 (2010).
31 Xu, R. H. et al. Basic FGF and suppression of BMP signaling sustain undifferentiated proliferation of human ES cells. *Nat Methods* 2, 185-190 (2005).
32 Ying, Q. L., Nichols, J., Chambers, I. & Smith, A. BMP induction of Id proteins suppresses differentiation and sustains embryonic stem cell self-renewal in collaboration with STAT3. *Cell* 115, 281-292 (2003).
33 Wobus, A. M. et al. Retinoic acid accelerates embryonic stem cell-derived cardiac differentiation and enhances development of ventricular cardiomyocytes. *J Mol Cell Cardiol* 29, 1525-1539 (1997).
34 Domian, I. J. et al. Generation of functional ventricular heart muscle from mouse ventricular progenitor cells. *Science* 326, 426-429 (2009).
35 Takahashi, K. et al. Induction of pluripotent stem cells from adult human fibroblasts by defined factors. *Cell* 131, 861-872 (2007).
36 Yu, J. et al. Induced pluripotent stem cell lines derived from human somatic cells. *Science* 318, 1917-1920 (2007).
37 Xu, C. et al. Feeder-free growth of undifferentiated human embryonic stem cells. *Nat Biotech* 19, 971-974 (2001).
38 Picht, E., Zima, A. V., Blatter, L. A. & Bers, D. M. SparkMaster: automated calcium spark analysis with ImageJ. *Am J Physiol Cell Physiol* 293, C1073-1081 (2007).

Citation of the above publications or documents is not intended as an admission that any of the foregoing is pertinent prior art, nor does it constitute any admission as to the contents or date of these publications or documents.

What is claimed is:

1. A composition comprising a mesodermal cell prepared in vitro and an exogenous agent that inhibits the retinoic acid signaling pathway in the mesodermal cell, wherein the retinoic acid signaling pathway of the mesodermal cell is inhibited by the exogenous agent thereby promoting ventricular cardiomyocyte formation from the mesodermal cell.

2. The composition of claim 1, wherein the mesodermal cell is differentiated in vitro from a pluripotent stem cell, a totipotent stem cell, a multipotent stem cell, an oligopotent stem cell, or a unipotent stem cell.

3. The composition of claim 1, wherein the mesodermal cell is differentiated in vitro from a mammalian stem cell.

4. The composition of claim 1, wherein the mesodermal cell is differentiated in vitro from a human stem cell.

5. The composition of claim 1, wherein the mesodermal cell is prepared in vitro by contacting a stem cell with at least one of basic fibroblast growth factor (bFGF), BMP 4 and activin A.

6. The composition of claim 1, wherein the mesodermal cell is prepared in vitro by contacting a stem cell with Wnt-3a, Bio, or CHIR99021.

7. The composition of claim 1, wherein the exogenous agent is selected from the group consisting of a retinoic acid antagonist, a retinoic acid receptor antagonist, and a retinoic X receptor antagonist.

8. The composition of claim 1, wherein the retinoic acid signaling pathway of the mesodermal cell is inhibited by contacting the mesodermal cell with the exogenous agent that reduces vitamin A, or by contacting the mesodermal cell with the exogenous agent that does not comprise vitamin A.

9. A cell culture medium, which comprises a population of cells differentiated in vitro from a mesodermal cell whose retinoic acid signaling pathway has been inhibited by an exogenous agent, wherein, without enrichment or isolation, at least 60% of the cells in the population are cardiomyocytes, and wherein at least 80% of the cardiomyocytes are ventricular cardiomyocytes.

10. The cell culture medium of claim 9, wherein at least 90%, at least 95%, at least 99%, or 100% of the cardiomyocytes in the cell population are ventricular cardiomyocytes.

11. The composition of claim 1, wherein the mesodermal cell is differentiated in vitro from an embryonic stem cell, an induced pluripotent stem cell, a fetal stem cell, or an adult stem cell.

12. The composition of claim 1, wherein the mesodermal cell is differentiated in vitro from a human embryonic stem cell or a human induced pluripotent stem cell.

13. The composition of claim 1, wherein the exogenous agent is a pan-retinoic acid receptor antagonist.

14. The composition of claim 1, wherein the exogenous agent is an inhibitor of retinoic acid synthesis.

15. The composition of claim 1, wherein the exogenous agent is selected from the group consisting of BMS-189453, AGN194310, AGN193109, Ro41-5253, SR11335, 9-cis-retinoic acid, disulfiram, and citral.

16. The composition of claim 1, wherein the exogenous agent is BMS-189453.

17. The composition of claim 1, further comprising a BMP antagonist.

18. The composition of claim 17, wherein the BMP antagonist is selected from the group consisting of a BMP 4 antagonist, Noggin, Chordin, Tsg, a BMP soluble receptor, BMPRIA, BMPRIB, and Dorsomorphin.

19. The composition of claim 1, further comprising a Wnt inhibitor.

20. The composition of claim 19, wherein the Wnt inhibitor is dickkopf homolog 1 (DKK1).

21. The composition of claim 1, further comprising a BMP antagonist and a Wnt inhibitor.

22. The composition of claim 21, wherein the exogenous agent is BMS-189453, the BMP antagonist is Noggin, and the Wnt inhibitor is dickkopf homolog 1 (DKK1).

23. The composition of claim 1, further comprising a culture medium with reduced or depleted vitamin A.

24. The composition of claim 1, wherein the mesodermal cell is prepared in vitro by culturing said mesodermal cell on a cell culture plate.

* * * * *